(12) United States Patent
Landsman et al.

(10) Patent No.: US 8,195,475 B1
(45) Date of Patent: Jun. 5, 2012

(54) METHOD FOR OPTIMALLY DETERMINING APPROPRIATE ERGONOMICS FOR OCCUPANTS OF A WORKSPACE

(75) Inventors: James Landsman, Grand Haven, MI (US); Sherman Robbins, Caledonia, MI (US); Douglas Gregory, Grand Rapids, MI (US); Drew Bossen, Iowa City, IA (US)

(73) Assignee: Atlas Ergonomics LLC, Grand Haven, MI (US)

( * ) Notice: Subject to any disclaimer, the term of this patent is extended or adjusted under 35 U.S.C. 154(b) by 2406 days.

(21) Appl. No.: 10/250,095

(22) Filed: Jun. 3, 2003

Related U.S. Application Data

(60) Provisional application No. 60/319,381, filed on Jul. 5, 2002, provisional application No. 60/319,291, filed on Jun. 3, 2002.

(51) Int. Cl.
*G06Q 10/00* (2006.01)
*G06Q 50/00* (2006.01)
(52) U.S. Cl. .................................. 705/2; 705/3
(58) Field of Classification Search .............. 705/2–3
See application file for complete search history.

(56) References Cited

U.S. PATENT DOCUMENTS

| | | | |
|---|---|---|---|
| 4,804,227 A * | 2/1989 | Hansen | 297/300.1 |
| 5,495,811 A | 3/1996 | Carson et al. | |
| 5,918,693 A | 7/1999 | Mantovani et al. | |
| 5,933,809 A * | 8/1999 | Hunt et al. | 705/3 |
| 6,039,392 A | 3/2000 | Dencker | |
| 6,692,435 B1 * | 2/2004 | Choate | 600/300 |
| 6,931,387 B1 | 8/2005 | Wong et al. | |
| 7,188,151 B2 * | 3/2007 | Kumar et al. | 709/217 |
| 2002/0095417 A1 | 7/2002 | Gordon | |
| 2002/0198473 A1 * | 12/2002 | Kumar et al. | 600/595 |

OTHER PUBLICATIONS

Huston, Dr. Ronald L., "Design Parameters for Comfortable and Safe Vehicle Seats", Society of Automotive Engineers, Feb. 24, 1997, Abstract Report.*

* cited by examiner

*Primary Examiner* — Jason Dunham
*Assistant Examiner* — Amber Altschul
(74) *Attorney, Agent, or Firm* — McGarry Bair PC

(57) ABSTRACT

A business method for optimally determining appropriate ergonomics of occupants of a workspace including a metric determined from personal-, environmental- and task-related attributes.

17 Claims, 34 Drawing Sheets

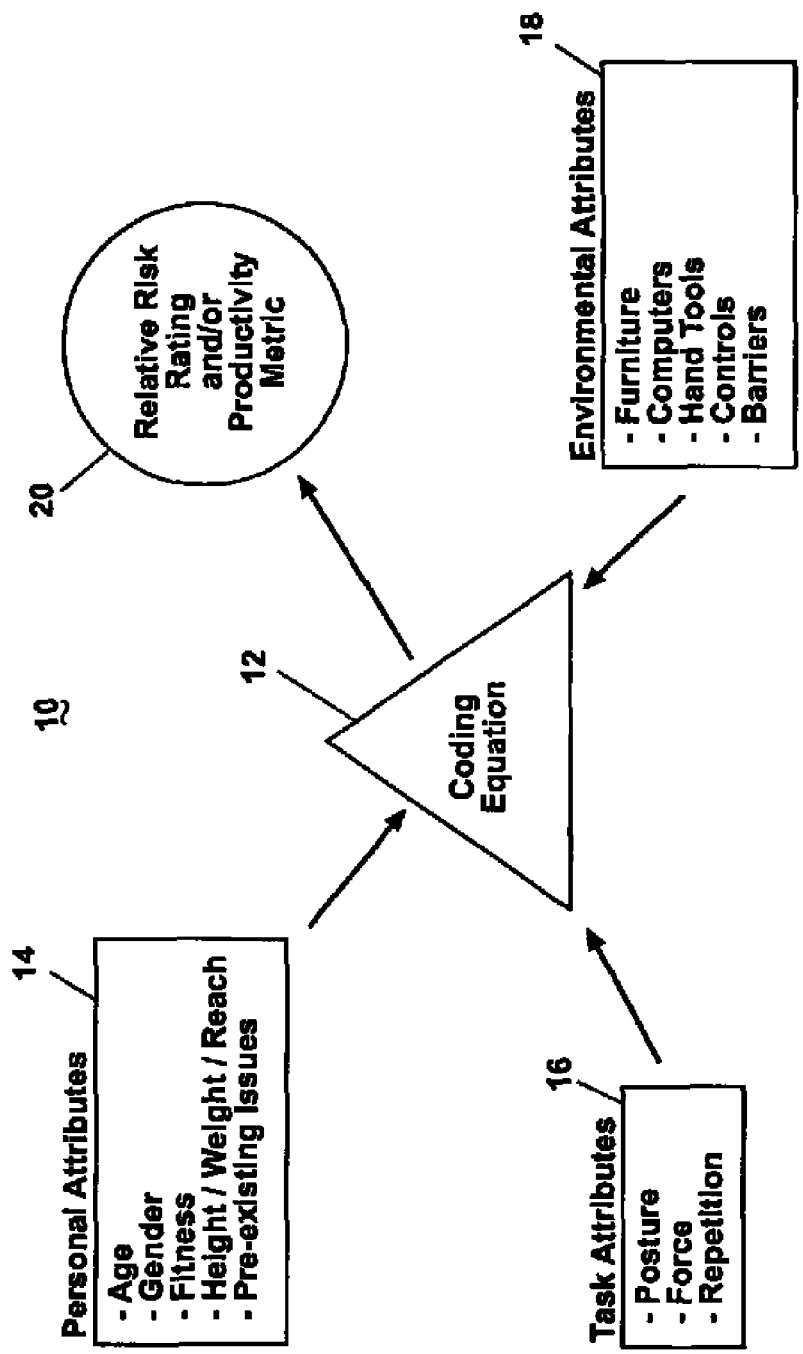

| Product | Injury Risk | Indirect Cost | Direct Cost | Product Cost | ROI | Fatigue Factor | Productivity |
|---|---|---|---|---|---|---|---|
| Product or Wkstn A | 0.50% | $67,500 | $22,500 | $4,800 | 25.00% | 0.975 | 102.50% |
| Product or Wkstn B | 2.00% | $67,500 | $22,500 | $3,800 | 12.50% | 0.997 | 100.30% |
| Product or Wkstn C | 3.00% | $67,500 | $22,500 | $3,000 | NA | 1.046 | 95.40% |

Fig. 1D

| Size Limitations | Standard Product | Limited Options | Big/Tall Product |
|---|---|---|---|
| Chairs | Product Dependendent / Product Dependendent | Product Dependendent / Product Dependendent | Product Dependendent / Product Dependendent |
| Height | | | |
| Weight | | | |
| Individual Risk | Low Risk | Moderate Risk | High Risk |
| Chairs | | | |
| Seat Height Adjustability | | x | x |
| Arm Height Adjustability | | x | x |
| Arm Width Adjustability | | x | x |
| Lumbar/Back Height Adjustability | | | x |
| Tilt Lock | | | x |
| Fitted Seat Pan or Seat Depth Adjustability | x | x | x |
| Seat Depth Adjustability | | Multi-user | Multi-user |
| Work Surface | | | |
| Set Height | Panel Hung | Panel Hung | Panel Hung |
| Pin Adjustable | Free Standing | Free Standing | Free Standing |
| Crank Adjustable | | Multi-user | Multi-user |
| Torsion Adjustable | | Multi-user | Multi-user |
| Electric Adjustable | | Optional | Optional |
| Sit to Stand | | | |
| Keyboard Mechanism | | | |
| Recommended | | x | x |
| Peripherals | | | |
| External Keyboard and Mouse | | | Laptop User |
| External Monitor | | Laptop User | Laptop User |
| Laptop or Monitor Riser | Situation Dependent | Situation Dependent | Situation Dependent |
| Document Holder | >2 hrs source document use | >2 hrs source document use | >2 hrs source document use |
| Task Light | >2 hrs source document use | >2 hrs source document use | >2 hrs source document use |
| Phone Head Set | >2 hrs telephone use | >2 hrs telephone use | >2 hrs telephone use |
| Foot Rest | | If feet do not rest on floor | If feet do not rest on floor |

Fig. 7

Worksurface Height-seated
1.00" increments

| Inches | scale | color |
|---|---|---|
| <=27.00 | | |
| 27.00 | 1.0 | orange |
| 28.00 | 3.0 | lavender |
| 29.00 | 5.0 | light yellow |
| 30.00 | 7.0 | blue |
| 31.00 | 9.0 | gold |
| 32.00 | 11.0 | green |
| >=32.00 | | |

Worksurface Height-standing
1.00" increments

| Inches | scale | color |
|---|---|---|
| TBD | | |
| TBD | 1.0 | orange |
| TBD | 3.0 | lavender |
| TBD | 5.0 | light yellow |
| TBD | 7.0 | blue |
| TBD | 9.0 | gold |
| TBD | 11.0 | green |
| TBD | | |

Seat Height
0.25" increments

| Inches | scale | color |
|---|---|---|
| <=15.00 | | |
| 15.00 | -1.0 | rose |
| 15.25 | -1.0 | rose |
| 15.50 | 0.0 | rose |
| 15.75 | 0.0 | orange |
| 16.00 | 1.0 | orange |
| 16.25 | 1.0 | orange |
| 16.50 | 2.0 | orange |
| 16.75 | 2.0 | lavender |
| 17.00 | 3.0 | lavender |
| 17.25 | 3.0 | lavender |
| 17.50 | 4.0 | lavender |
| 17.75 | 4.0 | light yellow |
| 18.00 | 5.0 | light yellow |
| 18.25 | 5.0 | light yellow |
| 18.50 | 6.0 | light yellow |
| 18.75 | 6.0 | blue |
| 19.00 | 7.0 | blue |
| 19.25 | 7.0 | blue |
| 19.50 | 8.0 | blue |
| 19.75 | 8.0 | gold |
| 20.00 | 9.0 | gold |
| 20.25 | 9.0 | gold |
| 20.50 | 10.0 | gold |
| 20.75 | 10.0 | green |
| 21.00 | 11.0 | green |
| >=21.00 | | |

Arm Height
0.50" increments

| Inches | scale | color |
|---|---|---|
| <=7.0 | 1.0 | orange |
| 7.00 | 1.0 | orange |
| 7.50 | 2.0 | orange |
| 8.00 | 3.0 | lavender |
| 8.50 | 4.0 | lavender |
| 9.00 | 5.0 | light yellow |
| 9.50 | 6.0 | light yellow |
| 10.00 | 7.0 | blue |
| 10.50 | 8.0 | blue |
| 11.00 | 9.0 | gold |
| >=11.00 | | |

Seat Depth
0.25" increments

| Inches | scale | color |
|---|---|---|
| <=17.00 | | |
| 17.00 | 1.00 | lavender |
| 17.25 | 1.00 | lavender |
| 17.50 | 2.00 | lavender |
| 17.75 | 2.00 | light yellow |
| 18.00 | 3.00 | light yellow |
| 18.25 | 3.00 | blue |
| 18.50 | 4.00 | blue |
| 18.75 | 4.00 | blue |
| 19.00 | 5.00 | blue |
| >=19.00 | 5.00 | blue |

Keyboard Height-seated
1.00" increments

| | | |
|---|---|---|
| <=-4.00 | | Red |
| -4.00 | | Yellow |
| -3.00 | | Green |
| -2.00 | | Yellow |
| -1.00 | | Yellow |
| 0.00 | | Red |
| >=0.00 | | Red |

Keyboard Height-standing
1.00" increments

| | | |
|---|---|---|
| <=-4.00 | | TBD |
| -4.00 | | TBD |
| -3.00 | | TBD |
| -2.00 | | TBD |
| -1.00 | | TBD |
| 0.00 | | TBD |
| >=0.00 | | TBD |

Keyboard Tilt
1 degree increments

| | | |
|---|---|---|
| <=0 | | Red |
| 0 degrees | | Yellow |
| -1 degrees | | Yellow |
| -2 degrees | | Yellow |
| -3 degrees | | Yellow |
| -4 degrees | | Yellow |
| -5 degrees | | Green |
| -6 degrees | | Green |
| -7 degrees | | Green |
| -8 degrees | | Yellow |
| -9 degrees | | Yellow |
| -10 degrees | | Yellow |
| -11 degrees | | Yellow |
| -12 degrees | | Yellow |
| >=-12 degrees | | Red |

Fig. 9

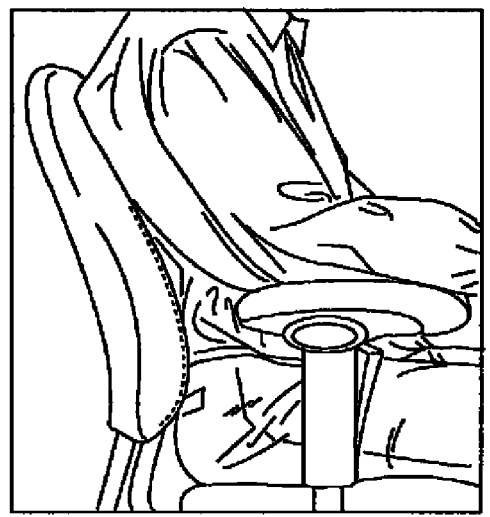
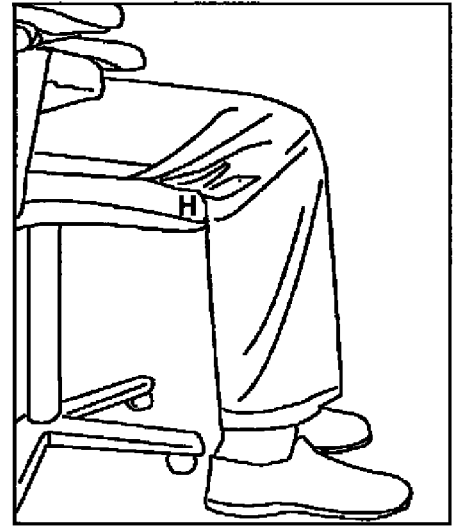
Fig. 28  Fig. 29
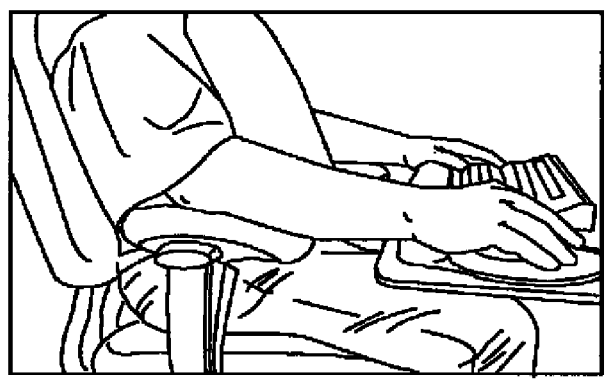
Fig. 30

Survey:

- How long is your typical workday?
  - < 2 hours
  - 2-4 hours
  - > 4 hours
  - > 8 hours
  - > 10 hours
- What percentage of your workday are you performing computing tasks?
  - <10%
  - 10-25%
  - 25-50%
  - 50-75%
  - >75%
- Beyond your work life, how many hours per day do you typically use the computer at home?
  - < 1 hour
  - 1-2 hours
  - 2-4 hours
  - > 4 hours
- With regards to work, who will be using your computer?
  - Single user (only me)
  - Multiple user (I share my computer with a co-worker)
- With regards to work, what kind of computer do you use?
  - Desktop computer
  - Laptop computer
  - Handheld computing / PDA's
- With regards to work, what kind of work will the computer be used for?
  - Word processing
  - Graphic design
  - Data entry
  - Surfing the net
  - Games
- Phone usage
  - Infrequent (0-10% of workday)
  - Occasional (10-33% of workday)
  - Frequent (33-66% of workday)
  - Constant (>66% of workday)
- Use of Source Document
  - Infrequent (0-10% of workday)
  - Occasional (10-33% of workday)
  - Frequent (33-66% of workday)
  - Constant (>66% of workday)

Fig. 48

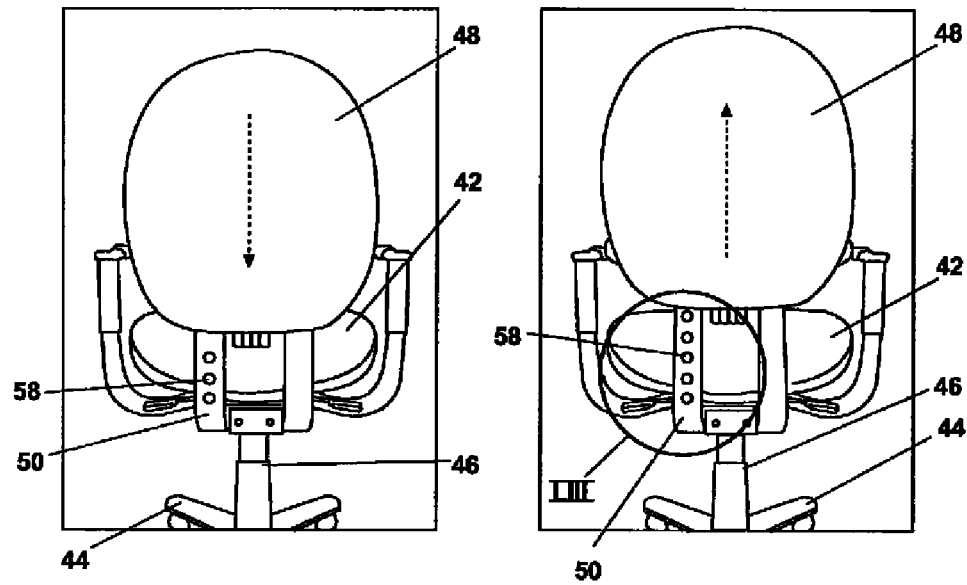
Fig. 51  Fig. 52
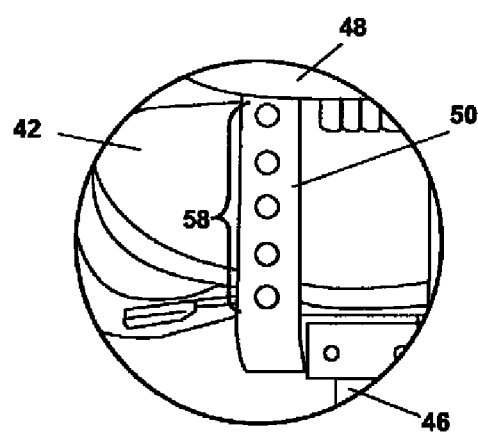
Fig. 53

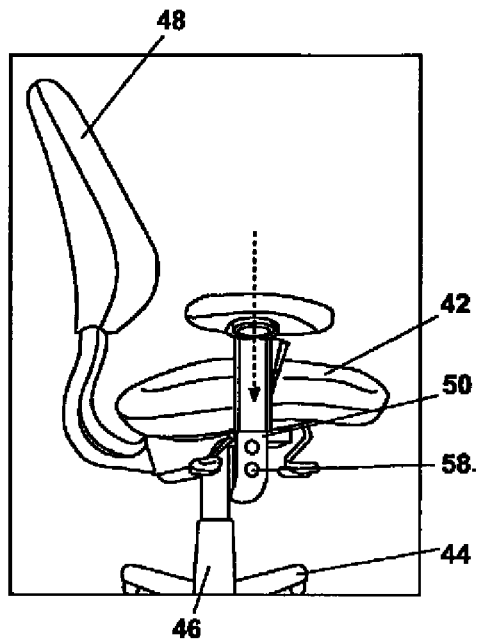 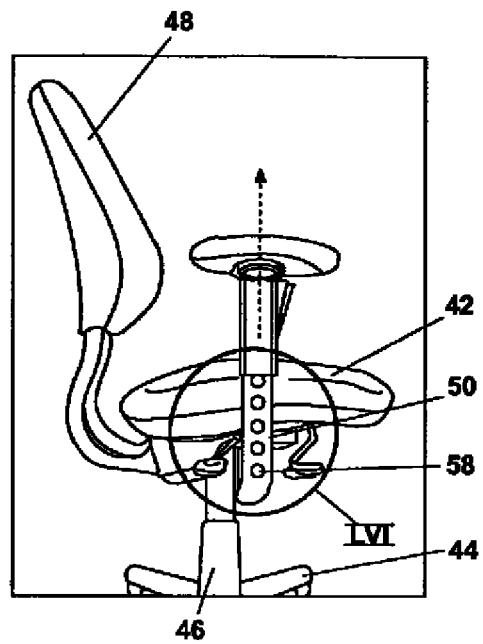
Fig. 54  Fig. 55
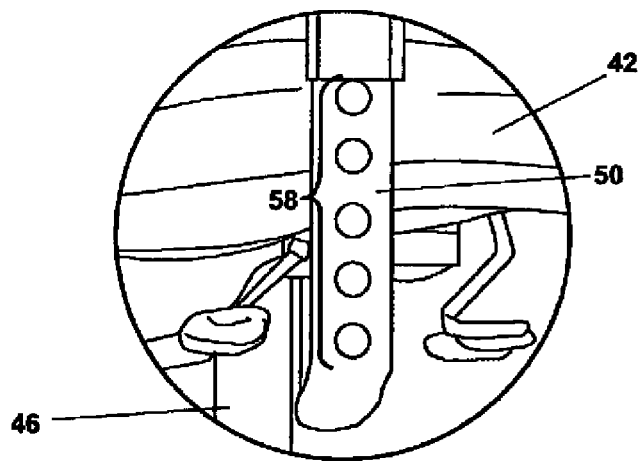
Fig. 56

METHOD FOR OPTIMALLY DETERMINING APPROPRIATE ERGONOMICS FOR OCCUPANTS OF A WORKSPACE

CROSS REFERENCE TO RELATED APPLICATIONS

This application claims the benefit of U.S. Provisional Application Ser. No. 60/319,291, filed Jun. 3, 2002, and U.S. Provisional Application Ser. No. 60/319,381, filed Jul. 5, 2002, both entitled "Method for Optimally Determining Appropriate Ergonomics for Occupants of a Workspace."

BACKGROUND OF INVENTION

1. Field of the Invention

In one aspect, the invention relates to a business method for optimally determining appropriate ergonomics of occupants of a workspace including a metric determined from personal-, environmental- and task-related attributes.

2. Description of the Related Art

Ergonomics have become an increasingly important concern in several industries and fields of endeavor. These industries include, but are not necessarily limited to, office furniture (including the wholesale and retail sale thereof), interior design, product identification and design, manufacturing equipment sale and design (both internal and "lean" manufacturing), and safety audit organizations which assess risk and audit compliance to ensure a safe working environment. Ergonomics are also important in the insurance industry in assessing risk, providing guidelines and auditing compliance with generally-accepted or industry-mandated policies.

Currently there are no standard ergonomics methods to evaluate the person (especially groups of people), their particular work-related task, and their environment (work station, assembly station, etc.). Although there exist various methods by which the ergonomics of one subset of the above categories are used, there are no integrated methods of assessing the ergonomics of a work-related environment. In addition, while an ergonomist might be able to quantify each of the above-identified categories (i.e., person, task and environment), it has not been done in a manner which can quantifiably define a risk in the interaction of those variables, and which can combine the quantified output with known incident rates and associated costs to provide information to determine what sort of return on investment (ROI) or increase in productivity a company might realize from an improvement in ergonomics.

The measurement of ergonomics has been attempted but has not yielded satisfactory results. Some companies have invested in methods to gather anthropometrical data on individual employees but this must be done on a person-by-person basis. Other companies have tried to evaluate the tasks each employee performs to obtain an estimate on the impact on an employee's ergonomics. These task evaluation tools vary in sophistication and complexity. Companies, which create the work environment (i.e. furniture, assembly equipment, etc.), have relied primarily on aesthetic differentiation and feature and functional differentiation. Some companies, as well as the Business & Institutional Furniture Manufacturer's Association (BIFMA), have developed individual ergonomic standards which have contributed to the design of individual ergonomic products.

These prior art ergonomics estimation tools have been "single-user" solutions at best. These tools have not focused on acquiring data on large groups of people and provide little in the way of proactive solutions focused on, company-based populations. In addition, most of these solutions are difficult to duplicate, require expertise to utilize, and are created and empowered by a small group of individuals within small populations focused on reactive intervention, e.g., the ergonomics solutions are implemented after a work-related or repetitive stress injury.

There is a general lack of integrated and systemic solutions that consider the person, their task, and their environment. ROI models have been viewed as either incomplete or lacking in sophistication. With regard to the determination of an ergonomics-related solution to personal or anthropometrical data on individuals in the workspace, this data has typically involved the comprehensive measurement of many individuals in the workspace or at least those individuals whose health needs are being addressed. The measurements are detailed, invasive and time consuming. A simpler, more intuitive, user-friendly system of inputting anthropometrical data is needed. In the past, broad-based data collection has been performed to provide statistical curves and probability information for general population anthropometric distribution. These broad-based methods are time-consuming. They do not meet individual employee needs, and it is often prohibitively expensive to capture a sufficiently large population sample to comprise a meaningful database.

With respect to the office furniture industry, ergonomics are an important consideration. Employees working in a particular workspace can suffer repetitive stress injuries and general discomfort when operating in an ergonomically-unbalanced environment. This can result in additional costs to a company, such as with lost workdays, lower productivity, workers' compensation claims and the like. It is desirable for companies to assess their ergonomics with respect to their office furniture, in their interior design and sale/purchase of furniture, identifying products which will result in better ergonomics, assessing corporate risks and managing safety, as well as in up-front product design. In addition to ensuring the optimal ergonomics of a company's workforce, the office furniture industry needs to differentiate its sales process and techniques as an opportunity to gain market share, create new market opportunities, and decrease the pressure on primarily using discounts to sell product. There is a growing need to assure a safe working environment in the office setting.

It is not known to define an ROI based on providing a safer work environment and productivity improvements gained through reducing fatigue within the office environment, and to provide a customer purchasing office furniture options based on that ROI data. In addition, once a company makes an office furniture purchasing decision, there is no current system to provide installation information on how to assure that an individual or a user group implements the ergonomically-based purchasing decisions with respect to settings and comfort positioning of the purchased office furniture.

It is also difficult to identify different ergonomic settings for a product. Many commercially-available office furniture products (see, e.g., the Aeron chair available from Herman Miller, Inc. and the Leap chair available from Steelcase) have numerous adjustments and settings to make their chairs fit a wide variety of users. However, companies purchasing these items have no criteria to determine whether the office furniture is an ergonomic fit for each user in the workspace. Further, there is no known user-friendly system proving customer safety and risk management teams the ability to audit and assure their employees are utilizing safe working habits (e.g., configuring their workspace to an optimal ergonomic fit). Rather, employees often simply configure a workspace to their personal, subjective preferences without regard to optimal ergonomics because employees typically do not know when their environment is ergonomically correct. This personal configuration dynamic is typically a result of a lack of feedback to office furniture manufacturers to guide product design to fill product niches based on data relevant to optimal workplace ergonomics. And, there is currently no industry-accepted system to validate the ergonomic claims of a product design.

Office furniture providers have tried to solve these problems by developing furniture standards (e.g., BIFMA Standards), and other less-accepted standards unique to a particular office furniture manufacturer. Companies have developed individual ergonomic products. Facilities teams have developed product evaluation and selection teams and processes to attempt to provide the best ergonomic fit for their workplace.

However, these attempts have not been pragmatic or useful. Most solutions are difficult to duplicate, require expertise to utilize, can conflict with other available solutions, and are created and empowered by a small group of individuals within small populations focused on reactive intervention (i.e., typically only after lost workdays and reduced productivity). There is no user-friendly approach, or known approaches are subjective to a particular workplace. Attempts to determine or model a customers ROI on an office furniture purchase have been viewed as either incomplete or lacking in sophistication and accuracy. Many companies avoid productivity-measurement issues that are product- or workstation-driven and ergonomic solutions have not been validated by outside entities to determine their validity or usefulness.

The same issues are prevalent in the office furniture retail industry. The office furniture retail sales industry (i.e. Staples, Office Max, etc.) needs to differentiate its sales process and techniques as an opportunity to gain market share and create new market opportunities. In addition, there is a growing need to assure a safe working environment in the home office setting due to the increased prominence of telecommuting and home-based businesses. There are even less options available to retail purchasers to define an ROI-based model to provide a safer work environment and for the retail sales outlet to provide to the customer purchase options based on that data. It is not known to define productivity improvement data gained through reducing fatigue within the home office environment, and to provide a purchasing customer equipment options based on that data. There is no known system to provide installation information on how to assure that the buyer implements ergonomic-based purchasing decisions. There is no known user-friendly system to easily identify different ergonomic settings for a product and to easily communicate those settings to a purchasing consumer (who may purchase a wide variety of products from different manufacturers). Companies have developed individual ergonomic products but they do not effectively communicate appropriate ergonomic settings to the consumer.

The same issues apply to other environments as well, such as a manufacturing workplace. No known technology or system exists to predict productivity improvements or risk reduction in the manufacturing environment based on ergonomic data of both the person performing tasks, the task, as well as the environment in which the task is performed. There is a growing need to assure a safe working environment in the manufacturing arena, which focuses on ergonomics and safe workplace design.

There is no known system to provide equipment installation information on how to assure that individual or user group implements any ergonomic-based purchasing decisions. There are no known user-friendly systems to be used by process designers, both internal and external to the manufacturer, to systematically consider optimizing the person(s), the task (s), and the environment. There is no known user-friendly system to easily identify different ergonomic settings for a product. There is no known user-friendly system providing customer safety and risk management teams the ability to audit and assure their employees are utilizing safe working habits. Further, there is no closed loop feedback system to guide product design to fill product niches based on ergonomic data identified in the workplace.

Providers of manufacturing equipment have attempted to develop individual ergonomic products for the manufacturing environment. Engineers have developed product evaluation and selection teams and processes as well as manufacturing task evaluation processes. Consultants have provided reactive intervention for specific individuals or settings (typically following injury or a period of reduced productivity). These past attempts have typically focused on single-user and company-based approaches.

These past attempted solutions are difficult to duplicate, require expertise to utilize, and are created and empowered by a small group of individuals within small populations focused on reactive intervention. There is no known user-friendly approach. The solutions exist, but are single-user solutions, typically subjectively designed for a particular workplace. Most companies avoid productivity-measurement issues that are product driven and any ergonomic solutions that have not been validated by outside entities.

These issues also exist in companies which desire to have so-called "safety audits" performed in their work environment (regardless of the particular field of endeavor of the company). Outside safety audit organizations as well as productivity-enhancement groups typically perform these audits to assess risk and audit compliance to attempt to ensure a safe working environment. These organizations include corporate risk and safety management groups, consultants to companies, governmental risk and safety management agencies, and labor unions.

Currently there are no known standard ergonomics methods to evaluate the person (especially groups of people), the task, and the environment (work station, assembly station, etc.), to combine those in a method that quantifiably defines the risk the interaction of those variables, and combines the output with known incident rates and associated costs to provide an associated dollar value for deviation from the optimum (or combines the output with known fatigue factors to predict any impact on productivity).

In order to attempt to provide more accurate and useful safety audits, some organizations have invested in methods to gather anthropometrical data on individual employees. A number of task evaluation tools exist, which vary in sophistication and complexity. Single-user solutions exist, which have not focused on acquiring data on groups of people, and provide little in the way of proactive solutions focused on company-based populations.

Most solutions are difficult to duplicate, require expertise to utilize, and are created and empowered by a small group of individuals within small populations focused on reactive intervention. There is a general lack of integrated solutions, which consider the person, task, and environment. ROI models have been viewed as either incomplete or lacking in sophistication. Finally, most companies avoid productivity-measurement issues that are product or workstation driven.

SUMMARY OF INVENTION

In one aspect, the invention relates to a business method for optimally determining appropriate ergonomics of occupants of a workspace including a metric determined from personal-, environmental- and task-related attributes.

The invention described herein is a user-friendly system to evaluate individuals and groups of individuals. A fully-integrated approach is provided that considers the person or persons, the task, and the environment of an employee's workspace. The invention contemplates the easy compilation of data to provide quantified risk assessment, ROI, and productivity impact. The ergonomic recommendations can be independently validated to ensure compliance and to prevent future ergonomic-related injury or productivity slowdowns.

The invention relates to an integrated, systematic approach to measure the attributes of the person, the task, and their environment, and to identify optimal outcomes and related ROI/productivity measures.

In one aspect, the invention relates to a method for optimizing the ergonomics of a workplace comprising the steps of: assessing a current ergonomic state of the workplace; comparing the current ergonomic state of the workplace to at least one predefined ergonomic standard; implementing at least one physical change to the workplace based on the comparing step; and optimizing the comparison step with data representative of the at least one implemented physical change. The at least one of ergonomics and productivity of the workplace are thereby improved by the at least one implemented physical change to the workplace and future ergonomic assessments and optimizations are continually improved by the optimizing step.

In another aspect, the invention relates to a system for improving the ergonomics for individuals in a workplace, the workplace comprising at least one item having at least one physically adjustable parameter, the system comprising: an assessment of at least one of: (1) the physical characteristics of a user, (2) the physical characteristics of at least one task performed by the user, and (3) the physical characteristics of at least one environmental feature of the workplace, wherein input data is created as a result of the assessment; and a determination of at least one of: (1) a preferred setting for the at least one physically adjustable parameter of the at least one item in the workplace based at least in part upon the input data created via the assessment, and (2) a recommended replacement item for the at least one item in the workplace having at least one physically adjustable parameter. The ergonomic data representative of the individuals in the workplace can thereby be evaluated during the assessment and the at least one physically adjustable parameter of the at least one item in the workplace can be positioned at a preferred setting based upon the results of the determination.

In an additional aspect, the invention relates to a system for optimally indicating preferred ergonomic positions for a work area having at least one physically adjustable parameter in a workplace comprising an indicator strip having a series of different ergonomic ranges thereon, wherein each ergonomic range corresponds to a preferred ergonomic positional range for a corresponding one of the at least one physically adjustable parameter of the work area, wherein a user working in the workplace can be positioned into a suitable ergonomic position simply by aligning each of the at least one physically adjustable parameters within the particular ergonomic range corresponding to that user.

In a further aspect, the invention relates to a method for optimally indicating preferred ergonomic positions for a work area having at least one physically adjustable parameter in a workplace comprising the steps of: providing an at least one indicator strip having a series of different ergonomic ranges thereon, wherein each ergonomic range corresponds to a preferred ergonomic positional range for a corresponding one of the at least one physically adjustable parameter of the work area; and applying the at least one indicator strip to the work area in a position so as to be in alignment with the at least one physically adjustable parameter of the workplace.

In another aspect, the invention relates to a method for optimizing the ergonomics of a workplace comprising the steps of: determining a health index relating to a current ergonomic state of the workplace; recommending at least one physical change to the current ergonomic state to a proposed ergonomic state based upon the determining step; predicting at least one of (1) a probability of injury, (2) a change in a probability of injury, (3) a change in productivity, and (4) a return on investment, as a result of the at least one physical change from the current ergonomic state to the proposed ergonomic state. Entities making decisions regarding the ergonomics of the workplace as well as purchasing decisions for the workplace can thereby be better educated as to the benefits of making the at least one physical change between the current ergonomic state and the proposed ergonomic state.

A plurality of embodiments of the various aspects of the invention are also contemplated.

The method can further comprise the step of surveying the ergonomic risk of an entity. The method can further comprise the step of surveying a health index of the entity. The method can further comprise the step of surveying user preferences based on at least one of fit, form and function of items used in the workplace. The method can further comprise the step of inventorying current furniture used by the entity. The method can further comprise the step of identifying high-risk individuals. The method can further comprise the step of holding a one-on-one consultation with any identified high-risk individuals. The method can further comprise the step of confirming that an individual is a high-risk through the one-on-one consultation. The method can further comprise the step of identifying necessary furniture for any confirmed high-risk individuals. The method can further comprise the step of identifying potential solutions to addressed the high-risk individuals.

The method can further comprise the step of defining at least one of an entity's risk of injury. The method can further comprise the step of optimizing a furniture investment for the entity. The method can further comprise the step of calculating fit settings for individual users of furniture in the workplace. The method can further comprise the step of providing a marking system on furniture located within the workplace. The method can further comprise the step of correlating calculated fit settings to the marking system used on the furniture.

The method can further comprise the step of training individuals working in the workplace on how to use furniture selected for each individual. The method can further comprise the step of recalibrating the fit of the selected furniture to each individual working in the workplace. The method can further comprise the step of monitoring at least one of the health and risk of injury of the entity associated with the workplace.

The method can further comprise the step of signaling a need to address an entity's risk level. The method can further comprise the step of continually refining the calculated fit settings for individuals in an entity's workplace. The method can further comprise the step of assessing at least one risk factor of users of the workplace. The method can further comprise the step of surveying the ergonomic risk of an entity. The method can further comprise the step of surveying a health index of the entity. The method can further comprise the step of correlating the ergonomic risk of the entity to the health index of an individual working in the workplace.

The method can further comprise the step of identifying high-risk individuals. The method can further comprise the step of defining at least one of an entity's risk and probability of injury. The method can further comprise the step of monitoring at least one of the health and risk of injury of the entity associated with the workplace. The method can further comprise the step of determining a change in the health index of an individual working in the workplace as a result of the at least one physical change implemented to the workplace. The method can further comprise the step of correlating the change in the health index to each of the at least one physical change implemented to the workplace.

The method can further comprise the step of determining which variables associated with the implemented change in the workplace are affected as a result of the implemented change. The method can further comprise the step of at least one of adjusting the weight of any affected active variables and adding new weighted variables as a result of the correlation step between the health index and the at least one physical change implemented to the workplace. The method can further comprise the step of creating a new individual risk definition equation as a result of the adjustment of the active variables and correlation of the individual health index. The method can further comprise the step of redefining at least one of an entity's risk and probability of injury using the newly-created individual risk definition equation.

The method can further comprise the step of recommending at least one item for use in the workplace by users of the workplace, wherein the recommended item has improved ergonomics over items previously used in the workplace. The method can further comprise the step of surveying a health index of the entity. The method can further comprise the step of inventorying items currently used by an entity in the workplace. The method can further comprise the step of correlating the determined health index to the inventory of items currently used by an entity in the workplace. The method can further comprise the step of proposing replacement items for those currently used by an entity in the workplace. The method can further comprise the step of optimizing the investment by an entity in the replacement items.

The method can further comprise the step of identifying high-risk individuals currently working in the workplace. The method can further comprise the step of identifying effective items for the identified high-risk individuals and which have improved ergonomics over those currently used by the entities in the workplace. The proposed replacement items can comprise furniture.

The method can further comprise the step of monitoring at least one of the health index and the risk of injury of an entity working in the workplace. The method can further comprise the step of correlating any change in the high-risk individual's health index to the recommended items on an item-by-item basis. The method can further comprise the step of identifying effective furniture types, characteristics and specific products for replacement of furniture items currently used by individuals in the workplace. The method can further comprise the step of prioritizing furniture solutions for any identified high-risk individuals.

The method can further comprise the step of improving the ergonomics of individuals in the workplace by correctly fitting them to items used in the workplace. The items used in the workplace can be furniture. The method can further comprise the step of measuring at least one physical characteristic of an individual who works in the workplace. The method can further comprise the step of calculating the individuals correct fit settings for an item used by the individual in the workplace. The method can further comprise the step of applying an indicator to the item used by the individual in the workplace indicating the fit settings for at least one adjustable parameter of the item used by the individual in the workplace. The indicator can indicate at least one satisfactory range of said settings for the at least one adjustable parameter of the item used by the individual in the workplace. The at least one satisfactory range for the indicator can be visually perceptible from a predetermined distance for auditing purposes.

The method can further comprise the step of recalibrating the fit settings of the furniture to the individual. The method can further comprise the step of correlating the fit settings of the item used by an individual in the workplace to at least one of an active and an inactive variable. The method can further comprise the step of creating a new fitting equation based upon at least one of the fit settings of the item used by an individual in the workplace as correlated to that individuals fit settings for the item used in the workplace. The method can further comprise the step of verifying the fit settings of the item used by the individual in the workplace based upon the new fitting equation.

The assessment can further comprise at least one survey having at least one criterion relating to at least one ergonomic feature of the workplace. The at least one criterion can be evaluated based upon a predetermined scale. Each individual can be scored according to their ratings provided in the survey. At least one of a health index and a risk of injury factor can be calculated for each individual in the workplace based upon their ratings provided in the survey. The assessments of individuals in the workplace can be evaluated to determined whether any individual is a high risk for injury.

The determination can further comprise an equation employing input data representative of at least one of: (1) the physical characteristics of a user, (2) the physical characteristics of at least one task performed by the user, and (3) the physical characteristics of at least one environmental feature of the workplace. The equation preferably produces a value representative of a preferred setting for the at least one physically adjustable parameter of the at least one item in the workplace.

The system can also include an indicator for application to the at least one item in the workplace, the indicator being representative of a range of settings applicable to the at least one physically adjustable parameter of the at least one item. The indicator can be marked with the preferred setting for the at least one physically adjustable parameter of the at least one item. The indicator can be color-coded for ranges of acceptable settings of the at least one physically adjustable parameter of the at least one item. The at least one item can comprise multiple physically adjustable parameters, each parameter having an indicator associated therewith. The color-coded ranges on the multiple items can each be correlated to a preferred setting for each of the physically adjustable parameters on each item, whereby a particular color on each of the indicators can be associated with an individual user of the at least one item. The at least one item can comprise at least one furniture item.

The at least one physically adjustable parameter can comprise at least one of the following items selected from the group of: seat height, arm height, monitor position, leg position, thigh position, arm width adjustment, lumbar/back height adjustment, tilt lock adjustment, seat depth adjustment, work surface height, keyboard height, mouse position, document holder position, telephone position, telephone use position, foot rest position, task light presence and position.

The system can also include a calculation of a return on investment of an entity improving its ergonomics according to the determination as well as an inventory of items currently used in the workplace. The inventory of items currently used in the workplace can further comprise a replacement inventory of at least one replacement item having at least one physically adjustable parameter capable of being positioned in a preferred ergonomic position for at least one user in the workplace.

The ergonomic ranges on the indicator strip can be visually perceptible from a distance to allow for easy visual auditing of the alignment of the at least one physically adjustable parameter of the work area with the particular ergonomic range pertaining to the particular user in the work area.

A determination of the particular ergonomic range for each user of the work area can be provided which can employ input data representative of at least one of: (1) the physical characteristics of a user, (2) the physical characteristics of at least one task performed by the user, and (3) the physical characteristics of at least one environmental feature of the workplace.

Each ergonomic range on the indicator strip can include sub-graduated areas corresponding to additional preferred ergonomic settings within the ergonomic range. The at least one physically adjustable parameter of the work area can comprise a plurality of different physically adjustable parameters, and the indicator strip further comprises a plurality of indicator strips varying in size corresponding to the particular physically adjustable parameter to which the particular indicator strip relates to provide a range of ergonomic positions for a plurality of users coded to each ergonomic range. Each user can be coded to a particular ergonomic range. Each user can be trained how to set each physically adjustable parameter in their work area to their coded ergonomic range. Each ergonomic range can be color-coded to be visually distinct from one another.

The method can further comprise the step of positioning the at least one physically adjustable parameter of the work area in alignment with one of the series of ergonomic ranges on the indicator strip. The method can further comprise the step of positioning each of the at least one indicator strips onto the work area wherein the location of each of the at least one indicator strip corresponds to a preferred ergonomic position for each of the at least one physically adjustable parameters of the work area.

The method can further comprise the step of determining which ergonomic range on the at least one indicator strip corresponds most accurately to a particular user. The method can further comprise the step of positioning a user working in the workplace into a suitable ergonomic position simply by aligning each of the at least one physically adjustable parameters within the particular ergonomic range determined for that user.

The method can further comprise the step of auditing of the alignment of the at least one physically adjustable parameter of the work area with the particular ergonomic range pertaining to the particular user in the work area.

The method can further comprise the step of confirming the predicted at least one of (1) a probability of injury, (2) a change in a probability of injury, and (3) a return on investment, after the at least one physical change is made to convert the workplace from the current ergonomic state to the proposed ergonomic state. The health index can be determined based upon at least one criterion. The at least one criterion can comprise a plurality of criteria.

The determining step can further comprise conducting a survey of at least one occupant of the workplace to assist in determining the health index. The method can further comprise the step of correlating responses to the survey to at least one of: OSHA recordable history, worker's compensation history, and a health index of an occupant of the workplace. The method can further comprise the step of integrating the correlating step into the predicting step.

The method can further comprise the step of proposing at least one implemented solution for making the change between the current ergonomic state and the proposed ergonomic state. The method can further comprise the step of correlating the at least one implemented solution to at least one of: future OSHA recordable incidents, future worker's compensation incidents, and a future health index of an occupant of the workplace. The method can further comprise the step of integrating the correlating step into the predicting step.

The method can further comprise the step of assessing a furniture inventory for the workplace. The method can further comprise the step of correlating options available in the furniture inventory to at least one of: OSHA recordable history, worker's compensation history, and a health index of an occupant of the workplace. The method can further comprise the step of integrating the correlating step into the predicting step.

The method can further comprise the step of proposing at least one implemented furniture change for making the at least one physical change between the current ergonomic state and the proposed ergonomic state. The method can further comprise the step of correlating the at least one implemented furniture change to at least one of: future OSHA recordable incidents, future worker's compensation incidents, and a future health index of an occupant of the workplace. The method can further comprise the step of integrating the correlating step into the predicting step.

BRIEF DESCRIPTION OF DRAWINGS

The following paragraphs generally describe the contents of the drawings provided herein.

FIG. 1 is a schematic illustrating a business method for producing a relative risk rating and/or a productivity metric from a calculation which receives personal attributes, task attributes and environmental attributes as inputs according to the invention.

FIG. 1D is a sample datasheet outlining sample results of the method and system of FIG. 1 showing an example of the numerical output defining the Percent Return on Investment of FIG. 1C.

FIG. 7 is a table illustrating furniture recommendations based on size limitations and an individual's risk as assessed in FIG. 4 if the site is installed or in FIG. 5 if the site is new;

FIG. 9 is table showing an exemplary marking system that correlates results from the furniture fitting in FIG. 8 to a color;

FIG. 28 is an example of a human form seated in an office furniture chair showing a back of the human form in a proper ergonomic position with respect to a back rest of the chair.

FIG. 29 is an example of a human form seated in an office furniture chair showing legs of the human form and a proper ergonomic position with respect to a front edge of a seat portion of the chair.

FIG. 30 is an example of a human form seated at a computer keyboard showing armrests of an office furniture chair and a keyboard support providing a proper ergonomic position to the arms of the human form.

FIG. 48 is an example of a survey used to quantify computing-related task attributes of the method described herein according to the invention.

FIG. 51 illustrates an office chair provided with an ergonomic marking system according to the invention, the example shown in FIG. 51 being related to a back rest height adjustment for the office chair, the back rest height being shown in a lowered position, wherein only a portion of the ergonomic marking is shown in FIG. 51.

FIG. 52 illustrates the office chair of FIG. 51, wherein the back rest height being shown in FIG. 52 is in a raised position wherein a greater portion of the ergonomic marking is shown in FIG. 52.

FIG. 53 is an enlarged elevational view of the region marked LIII in FIG. 52.

FIG. 54 illustrates an office chair provided with an ergonomic marking system according to the invention, the example shown in FIG. 54 being related to an armrest height adjustment for the office chair, the armrest height being shown in a lowered position wherein only a portion of the ergonomic marking is shown in FIG. 54.

FIG. 55 illustrates the office chair of FIG. 54, wherein the armrest height being shown in FIG. 55 is in a raised position, wherein a greater portion of the ergonomic marking is shown in FIG. 55.

FIG. 56 is an enlarged elevational view of the region marked LVI in FIG. 55.

DETAILED DESCRIPTION

Figure 1A:
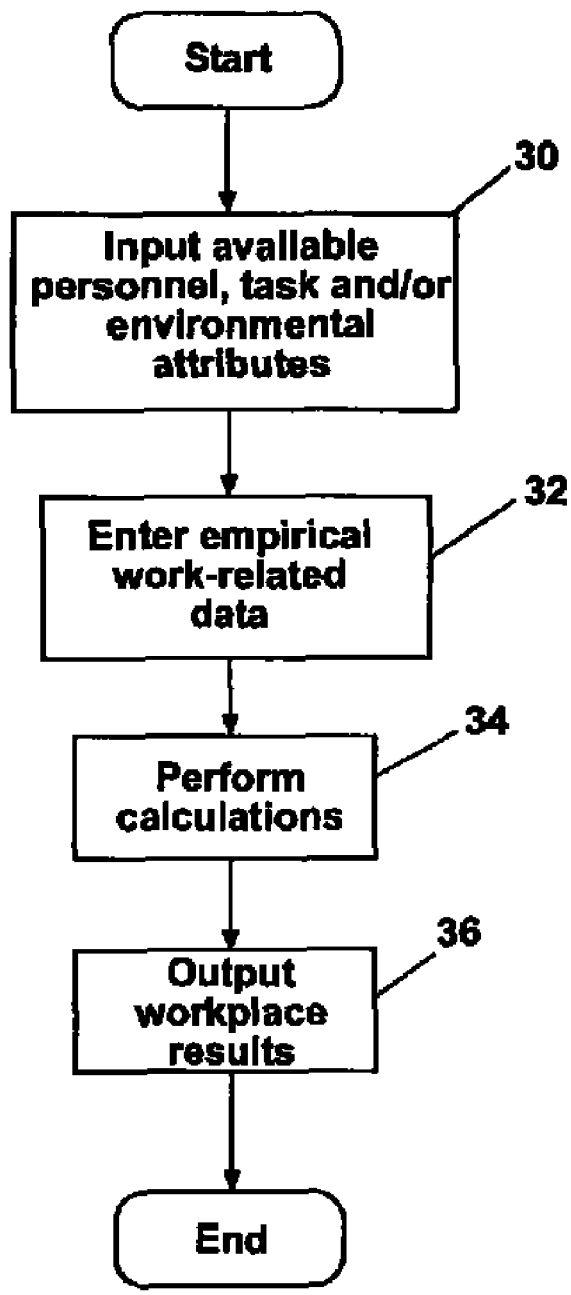
FIG. 1A is a flow chart illustrating general method steps embodied in the schematic of the invention shown in FIG. 1.

Referring now to the drawings and to FIG. 1 in particular, a system and method for optimally determining appropriate ergonomics for occupants of a workspace is shown generally by reference numeral 10. The system/method 10 preferably comprises a coding equation 12 which receives at least one of personal attributes 14, task attributes 16 and environmental attributes 18 relating to occupants of the workspace and their job-related tasks.

The personal attributes 14 can include various input values and parameters for workers in the workspace. These personal attributes 14 can include, but are not limited to: age, gender, fitness, height, weight, reach, and pre-existing conditions (such as the existence of a repetitive-stress injury such as carpal tunnel syndrome).

The task attributes 16 can include various input values and parameters for tasks performed by workers in the workspace. These task attributes 16 can include, but are not limited to: posture, perceived forces, and repetition of work-related functions and tasks.

The environmental attributes 18 can include various input values and parameters for the workspace itself. These environmental attributes 18 can include, but are not limited to: furniture types and positioning, computers, hand tools, controls and barriers.

A tangible benefit of this system and method 10 is the production of an output value 20 which relates to a relative risk rating and/or a productivity metric. The risk rating is designed to provide an indication of a worker's likelihood of encountering a work-related injury as a result of the attributes 14-18. This value can be expressed as a probability, a percentage or simply as an ordinal indicator (such as "Low", "Moderate", "High" or "Very High"). The productivity metric is designed to provide an indication of the potential for an increase or decrease in productivity as a result of the attributes 14-18. This value can be expressed as a percentage, a revenue change, a measure of lost workdays or simply an ordinal indicator (e.g., "No Change", "Decrease", or "Increase").

Turning to the flow chart shown in FIG. 1A, the method 10 associated with this invention is described in greater detail. As illustrated in step 30, the method 10 contemplates the input of personal attributes 14 (e.g., anthropometric data, gender, height, weight, ADA issues/physical handicaps, hand strength, general fitness, vision requirements, existing chronic conditions, age, hand dominance, recent pregnancy), task attributes 16 (e.g., keyboard-based, mouse-based, duration and percentage of time of task, upper extremity postures, wrist deviations, supported/unsupported upper extremities, sitting posture, casual, moderate or intense office use, PC vs. laptop use, force, repetition) and environmental attributes 18 (e.g., light and glare, relative position of the monitor, seating height/depth, adjustable height and width of arms, lumbar support, tilt and tension, caster relationship to floor surface, table height and depth, reach zones, vision zones, hand dominance and work style [left to right or right to left], knee swing space, elbow swing space).

As shown in step 32, empirical data can also be provided as an input to the method 10. For example, this empirical data can include, but is not limited to, the Occupational Safety and Health Administration (OSHA) log case rate for Cumulative Trauma Disorders (CTDs) or Musculo Skeletal Disorders (MSDs) or Repetitive Stress Injuries (RSIS), lost workdays, lost workday cases, case rates, national data for medical costs, and churn rate data.

At step 34, calculations are performed on the input data provided in steps 30 and 32. These calculations, which form the resulting output 20 shown in FIG. 1, can include a classification based on the personal attributes 14, the task attributes 16, and the environmental attributes 18, as well as a relational map of the three attribute areas 14-18 compared to an optimal point.

At step 36, the results of the calculation step 34 are provided. The output of step 36 can include, but is not limited to, options for moving closer to the optimal point determined in step 34, risks and costs of those options, and an evaluation of an expected risk of injury based on those costs and expected benefits.

Figure 1B:
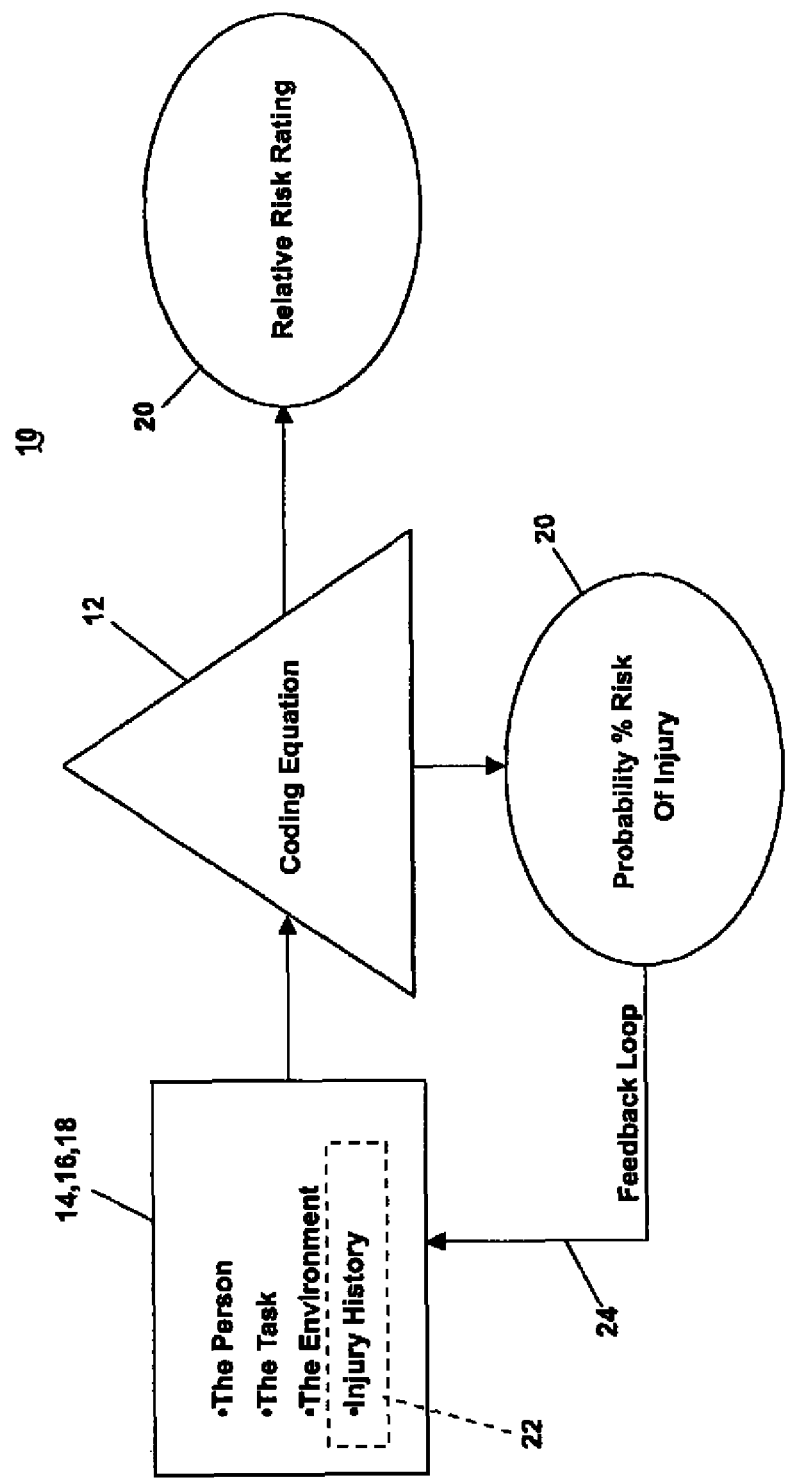
FIG. 1B is a schematic illustrating another embodiment of the business method and system of FIG. 1 including a feedback loop for continually enhancing the produced output of the method and system.

FIG. 1B shows an enhanced embodiment of the method and system 10 of FIG. 1. In this embodiment, an injury history 22 of a person (or group of people) is added as an input to the coding equation 12 (in addition to the personal, task and environmental attributes 14, 16 and 18 described above and in greater detail below). As can be seen in FIG. 1B, the coding equation 12 receives these inputs 14, 16, 18 and 22 and outputs a metric such as a relative risk rating and/or a probability/risk of injury (e.g., expressed in a percentage), each shown generally by reference numeral 20. In the embodiment of FIG. 1B, when a risk of injury metric is calculated, this information can be fed back (such as by the sample feedback loop 24 in FIG. 1B) to the input attributes 14, 16, 18 and 22 to further refine these input attributes.

The recent injury history 22 can focus on both current levels of pain and discomfort and work-related injury history. If a person acknowledges a work-related injury history (which includes, but is not limited to, an OSHA-recorded event), additional inputs can be provided by the person explaining the type of task and environment that attributed to the event.

In this manner, the invention contemplates a regression-type analysis that is incorporated into either the coding equation 12 or the formation and calculation of the input attributes 14, 16, 18 and 22. This can result in greater accuracy and prediction of the method and system 10 as a historical set of data for a person or group of people is assembled.

Figure 1C:
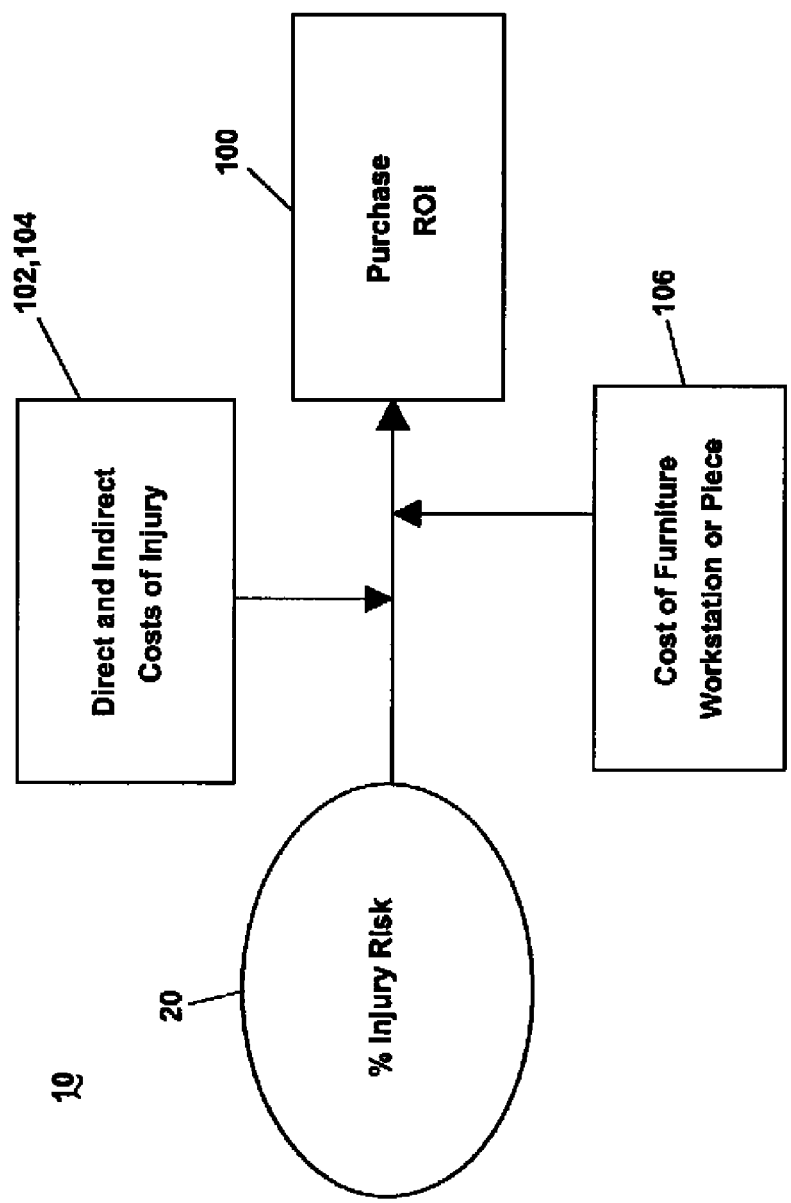
FIG. 1C is a schematic illustrating a tangible benefit of the method and system of FIG. 1 including the calculation of a Percent Return on Investment metric.

FIG. 1C is a schematic illustrating a tangible benefit of the method and system 10 of FIGS. 1-1B including the calculation of a Percent Return on Investment (ROI) metric 100. The risk of injury metric 20 described with respect to FIGS. 1-1B can be combined with indirect and direct costs of injury 102 and 104, respectively, as well as with a cost of an item 106. In this manner, the costs associated with injury and the probabilities associated therewith can be evaluated in connection with the simple product cost to determine whether the purchase of the item 106 is cost-effective.

FIG. 1D is a sample datasheet 110 outlining sample results of the method and system 10 of FIGS. 1-1C showing an example of the numerical output defining the Purchase Return on Investment of FIG. 1C. As can be seen, the datasheet 110 includes several columns of data, including: injury risk 20, indirect cost 102, direct cost 104, product cost 106, Return on Investment, Fatigue Factor and Productivity (collectively referred to with reference numeral 100).

The injury risk 112 is derived from the regression applied to historical data with respect to the particular product at issue in the particular row of the datasheet 110. This data can be determined from the refinement of the product database based on past history of individuals.

The direct cost 104 typically can be received from actuarial or insurance company data that defines the average medical cost for an incident or injury encountered with a particular product and/or workplace.

The indirect cost 102 is a multiple of the direct cost 104 based on actuarial or industry studies. The actual ratio of indirect cost 102 to direct cost 104 typically varies from 3:1 to 10:1. The indirect cost 102 attempts to quantify the consequential costs of an injury as opposed to the direct costs which typically quantify the out-of-pocket costs associated with the injury.

The product cost 106 can be supplied by the manufacturer of a specific product or workstation layout. This may be discounted and the discount may be input by either the manufacturer or the dealer/sales person.

The final three columns 100 of the datasheet are metrics output by the coding equation 12 described with respect to FIGS. 1-1C. These are the values to be considered by a potential purchaser of an item 106.

The work-related injury history 22 and associated inputs that define the cause of the injuries are used to continually refine the calculations in the coding equation 12 for each variable, and through the use of the data, the output metric 20 can predict the probability of an injury occurrence. The predicted probability of an injury will also be applied to different items and/or environments (such as office layouts or for individual pieces of furniture).

The predicted injury rate and cost for each product or from a base option is then combined with the average indirect and direct cost of the injury to define a Return On Investment for the buying options of the items 106 (as illustrated in the sample datasheet 110 of FIG. 1D).

Figure 2:
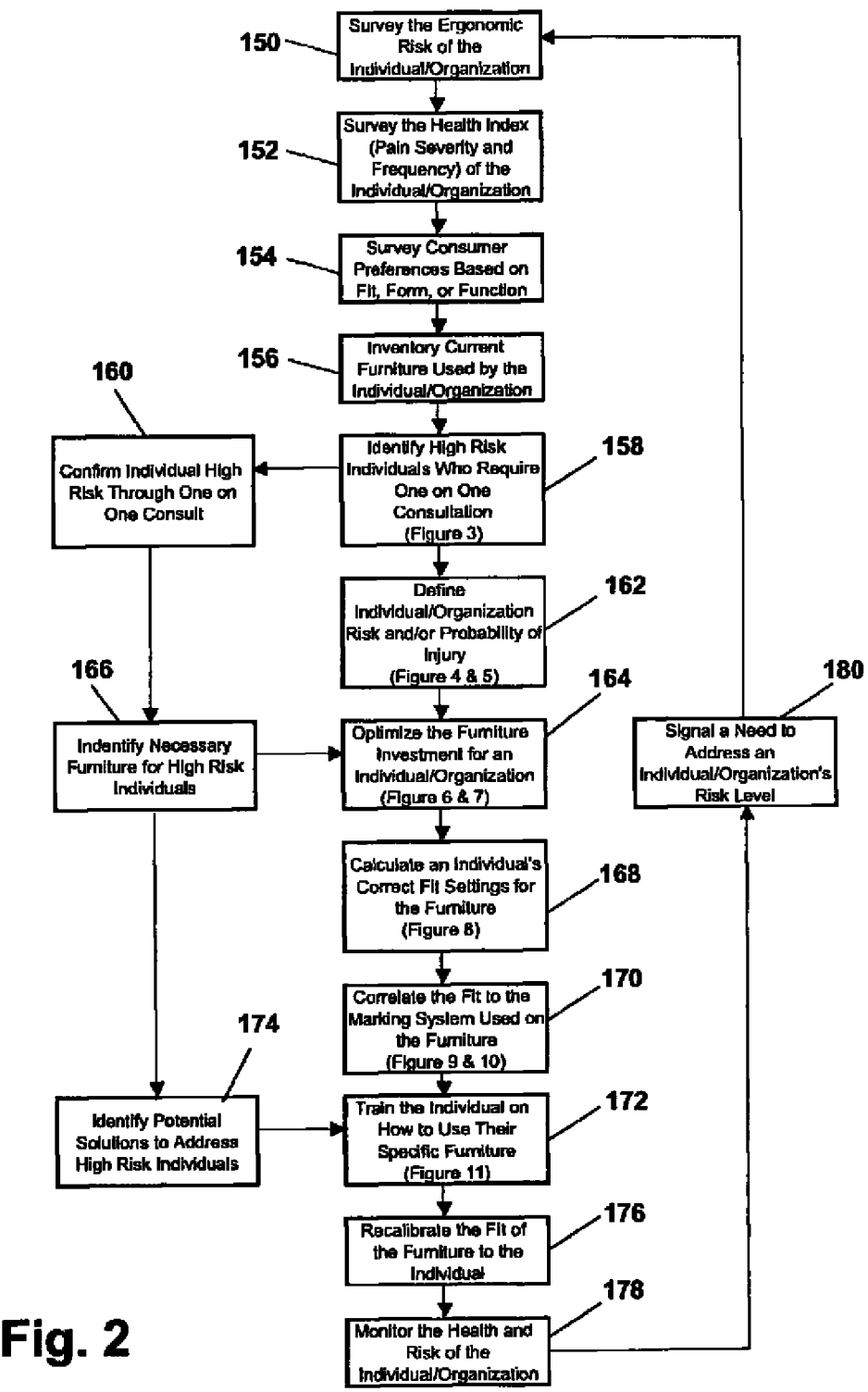
FIG. 2 is a schematic illustrating detailed method steps of another embodiment of the business method shown in FIG. 1.

A more detailed embodiment of the system and method 10 for optimally determining appropriate ergonomics for occupants of a workspace is illustrated in FIG. 2. The system 10 can be employed for both existing and new sites and generally begins with an assessment of the site. The assessment can involve several steps, such as surveying 150 the ergonomic risk of an organization or individuals within the organization and surveying 152 the health index of the organization or the individuals. As in the previous embodiment, ergonomic risk is related to the probability of an injury or loss in productivity due to improper ergonomic work conditions. The health index, which will be addressed in more detail hereinafter, is a function of pain severity and pain frequency.

Assessment can further include creating an inventory 156 of furniture or equipment currently utilized by the organization or individual and surveying 154 consumer preferences based on, for example, how furniture fits, how desirable its appearance is, and how it is operated or adjusted. The assessment steps can be performed in any logical order provided that information regarding the personal attributes 14, task attributes 16, and environmental attributes 18 is amassed for analysis.

Figure 3:
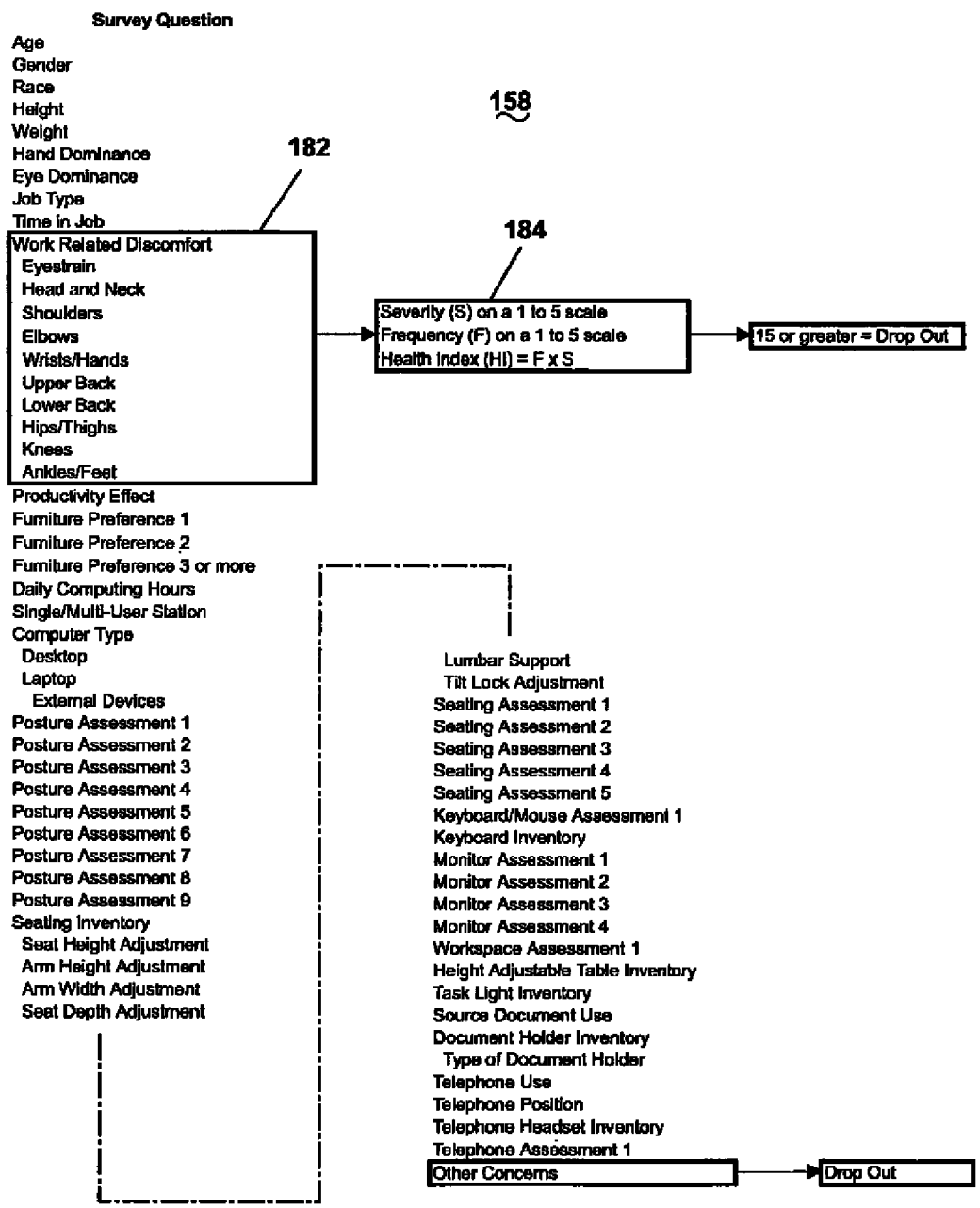
FIG. 3 is a list of exemplary survey topics that can be addressed to identify individuals who require a one on one consultation during implementation of the business method in FIG. 2.

During assessment, individuals who are at a high risk for ergonomic-related injuries and might require a one on one consultation are identified in step 158 with the aid of survey topics, a list of which is presented in FIG. 3. The survey topics relate to the various personal attributes 14, task attributes 16, and environmental attributes 18. The list in FIG. 3 is only representative, and it is within the scope of this invention to use other survey topics that assist in identifying high-risk individuals. Furthermore, an organization can define their own survey topics and imbed them into this survey and into all surveys employed in the system and method 10. This is a cost effective means for an organization to ask several individuals any number of survey questions. Examples of survey topics associated with work-related discomfort are given in box 182. The individual rates the severity (S) of pain and the frequency (F) of pain on a scale, for example from 1 to 5, wherein 5 is the most severe and most frequent. As shown in box 184, the health index (HI) is calculated by multiplying S by F, and if the HI is greater than a threshold value, for example 15, then the individual is identified as high risk. Alternatively, an individual can have concerns, labeled as "other concerns" in FIG. 3, that cause the individual to automatically be ascribed as high risk regardless of S, F, or a combination thereof.

The status of a high-risk individual is confirmed/rejected in the one on one consultation in step 160. During the one on one consultation, the personal attributes 14, task attributes 16, and environmental attributes 18 for the individual are recorded and analyzed. The analysis, which will be described in more detail hereinafter, provides a list of necessary furniture, as in step 166, or potential non-furniture solutions, as in step 174, for the high-risk individual. After implementation of the furniture and solutions, a client can use the previously recorded attributes 14, 16, and 18 in conjunction with new attributes to determine if there are any changes in the health index as a result of the new furniture and/or potential non-furniture solutions.

Figure 4:
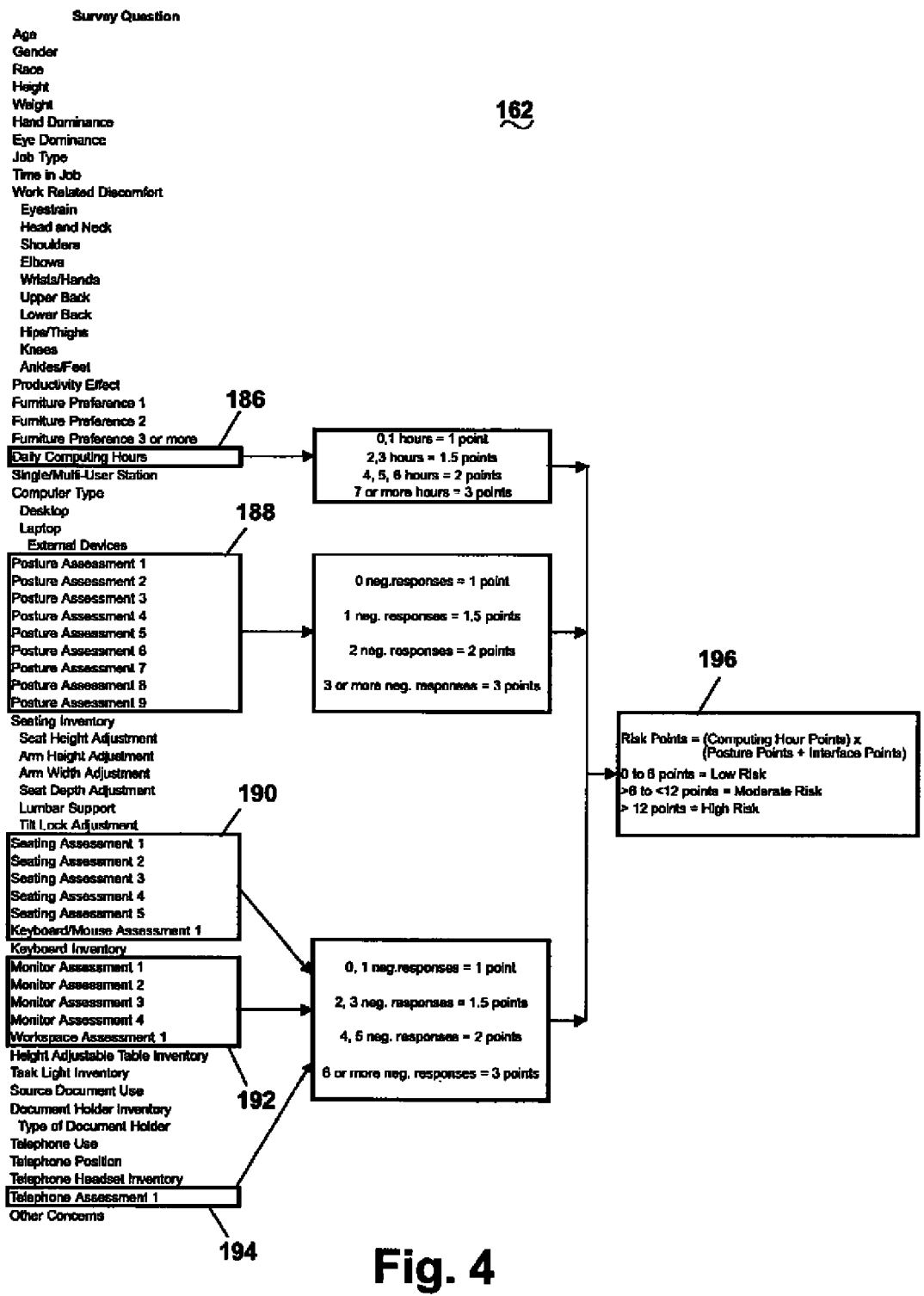
FIG. 4 is a list of exemplary survey topics that can be addressed in a risk assessment of an installed site during implementation of the business method in FIG. 2.

The information collected in the survey 150 of the ergonomic risk of the organization or individual is utilized to define ergonomic risk and/or probability of injury in step 162. Potential survey topics for an installed, already existing site are listed in FIG. 4. Again, the survey topics relate to the various personal attributes 14, task attributes 16, and environmental attributes 18. The list in FIG. 4 is provided for exemplary purposes, and it is within the scope of this invention to use other survey topics that assist in ergonomic risk assessment of a site. For example, computing hours, posture, seating, monitor, and telephone assessments are listed in boxes 186, 188, 190, 192, and 194, respectively. The latter three groups are collectively referred to as an interface assessment. Points are assigned to the organization or individual depending on the organization's or individual's responses to the survey topics. For example, an individual who spends 3 hours per day on the computer is assigned 1.5 points. Further, if an individual does not have proper posture for 2 posture assessments, then 2 points are assigned. Similarly, if the interface assessment yields 3 negative responses, then 1.5 points are assigned. The points from each group are then input into a function, such as the exemplary function in box 196, to calculate a metric, such as a probability or an overall risk point value, which can correspond to an ordinal indicator, similar to that described in the first embodiment. In the above example, the overall risk point value is 5.25, which corresponds to "low risk."

Figure 5:
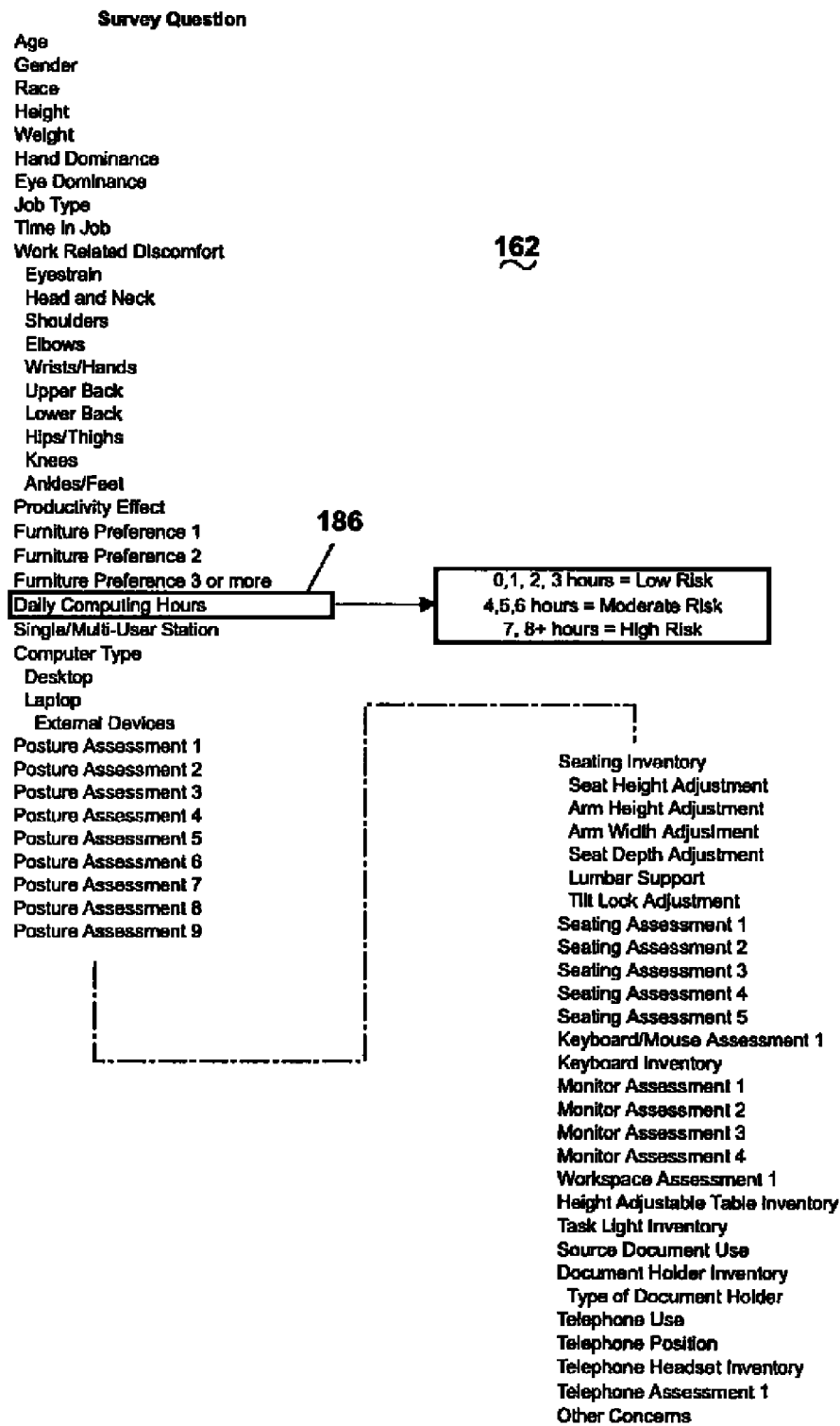
FIG. 5 is a list of exemplary survey topics that can be addressed in a risk assessment of a new site during implementation of the business method in FIG. 2.

Potential survey topics for a new site are listed in FIG. 5, which is identical to the list in FIG. 4. However, in assessing a new site, some of the survey topics are not applicable, such as posture assessment, because the furniture required to make the assessment does not exist. The ergonomic risk must be determined by relevant factors, such as daily computing hours 186. For example, if an organization or individual spends 6 hours per day on a computer, then their ergonomic risk is defined as "moderate."

Figure 6:
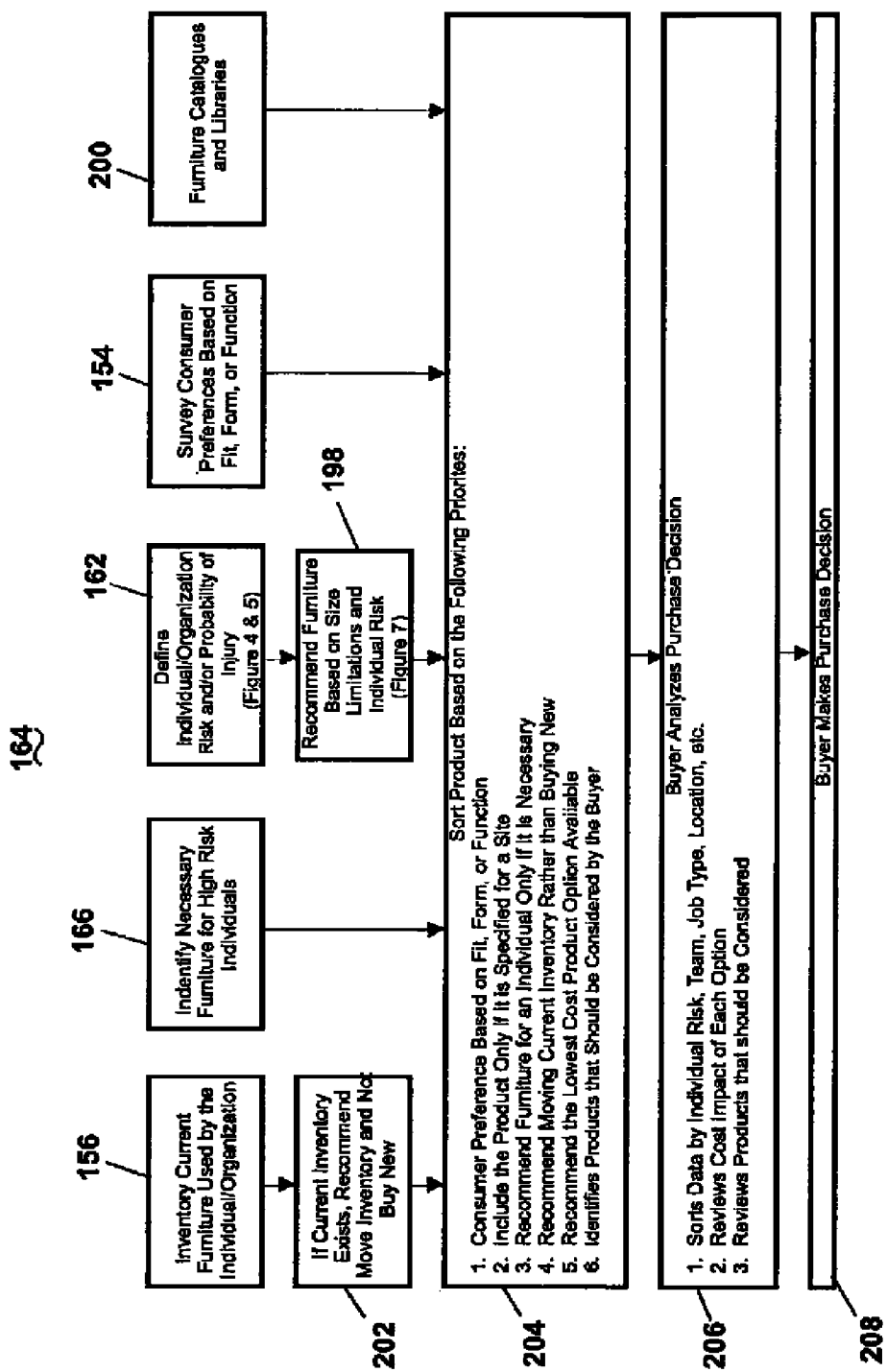
FIG. 6 is a schematic illustrating a furniture optimization process as employed in the business method in FIG. 2.

Once the assessment portions (steps 150-162) of the system and method 10 are completed, the furniture investment is optimized for an individual or organization in step 164, shown in FIG. 6. In this optimization process 164, inputs determined in step 156 (inventory of current furniture), step 166 (identification of necessary furniture for high-risk individuals), and step 154 (survey of consumer preferences) are combined with furniture catalogs and libraries 200 and recommendations 198 based on size limitations and individual risk. The recommendations 198, examples of which are shown in a table in FIG. 7, identify furniture items and accessories for organizations or individuals having various ergonomic risk levels, as defined in step 162, or physical size limitations. According to FIG. 7, for example, it is recommended that a moderate risk individual use a chair that has a tilt lock and adjustable seat height, arm height, arm width, lumbar/back height, and seat depth. Meanwhile, a chair for a low risk individual is required to have only an adjustable seat height.

In step 202, if the current inventory of furniture contains already contains appropriate items, then it is recommended that the current furniture is utilized rather than replacing it with new furniture. However, if recommended furniture is not in the current inventory, a list of suggested products for purchase is created from the inputs listed in the previous paragraph and sorted based on the priorities listed in FIG. 6 for step 204. Subsequently, in step 206, the organization or individual analyzes a purchase decision utilizing criteria shown in FIG. 6 to ultimately make the purchase decision in step 208. The priorities and criteria shown in steps 204 and 206, respectively, are exemplary, and other priorities and criteria can be employed in the furniture investment optimization process 164.

Once the furniture and other equipment has been selected and purchased, an individual's fit settings for the purchased furniture and current furniture are calculated in step 168. During furniture fitting 168, the individual's responses to survey topics are input into functions to compute the calculated settings for various aspects of the furniture. Examples of functions and rules for rounding the output of the functions are presented in box 210 of FIG. 8. The functions are developed from ergonomic engineering research and, as further research is conducted, can be altered, deleted, appended, or otherwise improved. In general, the functions are mathematical expressions of the relationship between fit settings and data resulting from the survey topics. If a survey topic is included in a function, then the survey topic is an active variable. Conversely, an inactive variable is a survey topic that is not a part of the mathematical expression.

The calculated settings are used to determine actual fit settings, as shown in boxes 212 and 214. The functions in box 212 are utilized if the work surface height is adjustable; however, if the work surface height cannot be raised or lowered, then the settings must account for the fixed height by using the functions in box 214. Again, the functions in boxes 212 and 214 are exemplary; they can be edited or otherwise improved, and it is within the scope of this invention to use furniture-fitting functions other than those in shown in boxes 212 and 214. Other considerations, such as overhead lighting distance, are addressed in box 216.

Figure 8:
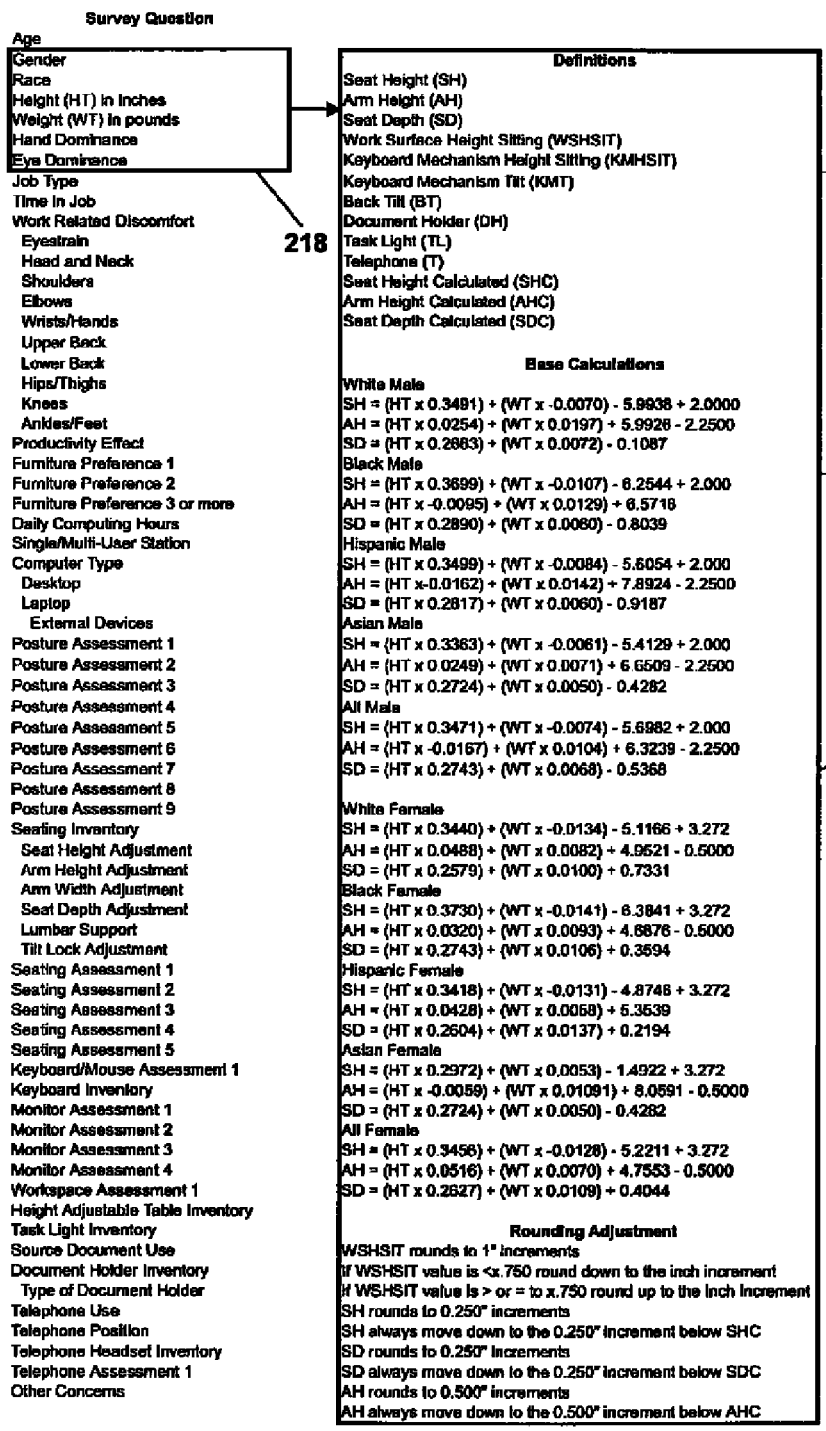
FIG. 8 is a list of exemplary survey topics that can be addressed in a furniture fitting and example of functions that can be utilized for the furniture fitting during implementation of the business method in FIG. 2.
Figure 8:
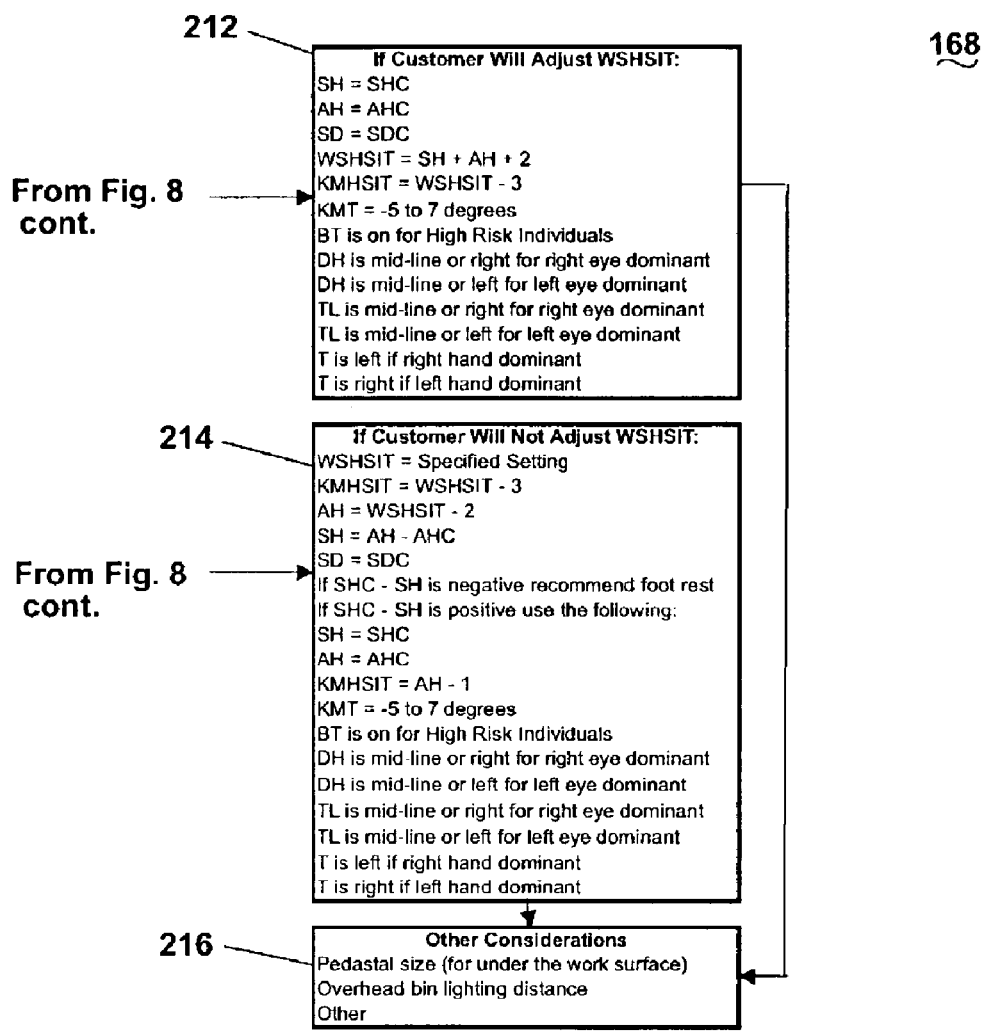

It has been determined that some fit settings can be calculated using responses from only a few survey topics, such as gender, race, height, weight, hand dominance, and eye dominance, which are highlighted in box 218 of FIG. 8. According to the functions in box 210, a chair's seat height (distance from the floor to the seat), arm height (distance from the seat to the arm), and seat depth can be determined from gender, race, height, and weight data. For example, a 25-year-old Asian male who weighs 165 pounds and is 70 inches tall has a calculated seat height, arm height, and seat depth of 19.1216, 7.3154, and 19.4648 inches, respectively, or 19, 7, and 19.25 inches after rounding, respectively. If the Asian male has an adjustable height work surface, then the actual fittings for the seat height, arm height, and seat depth are as calculated. The seated work surface height is 28 inches, and the keyboard mechanism is located 3 inches therebelow. Additionally, if the Asian male is right-handed and right eye dominant, then the document holder and task light should be mid-line or to the right and the telephone should be on the left.

Figure 10:
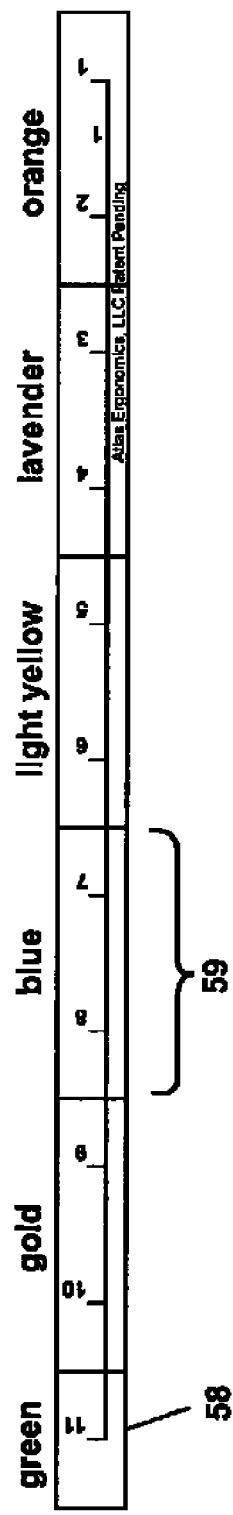
FIG. 10 is an example of a label that can be placed on a workspace and used in conjunction with the marking system in FIG. 9.
Figure 11:
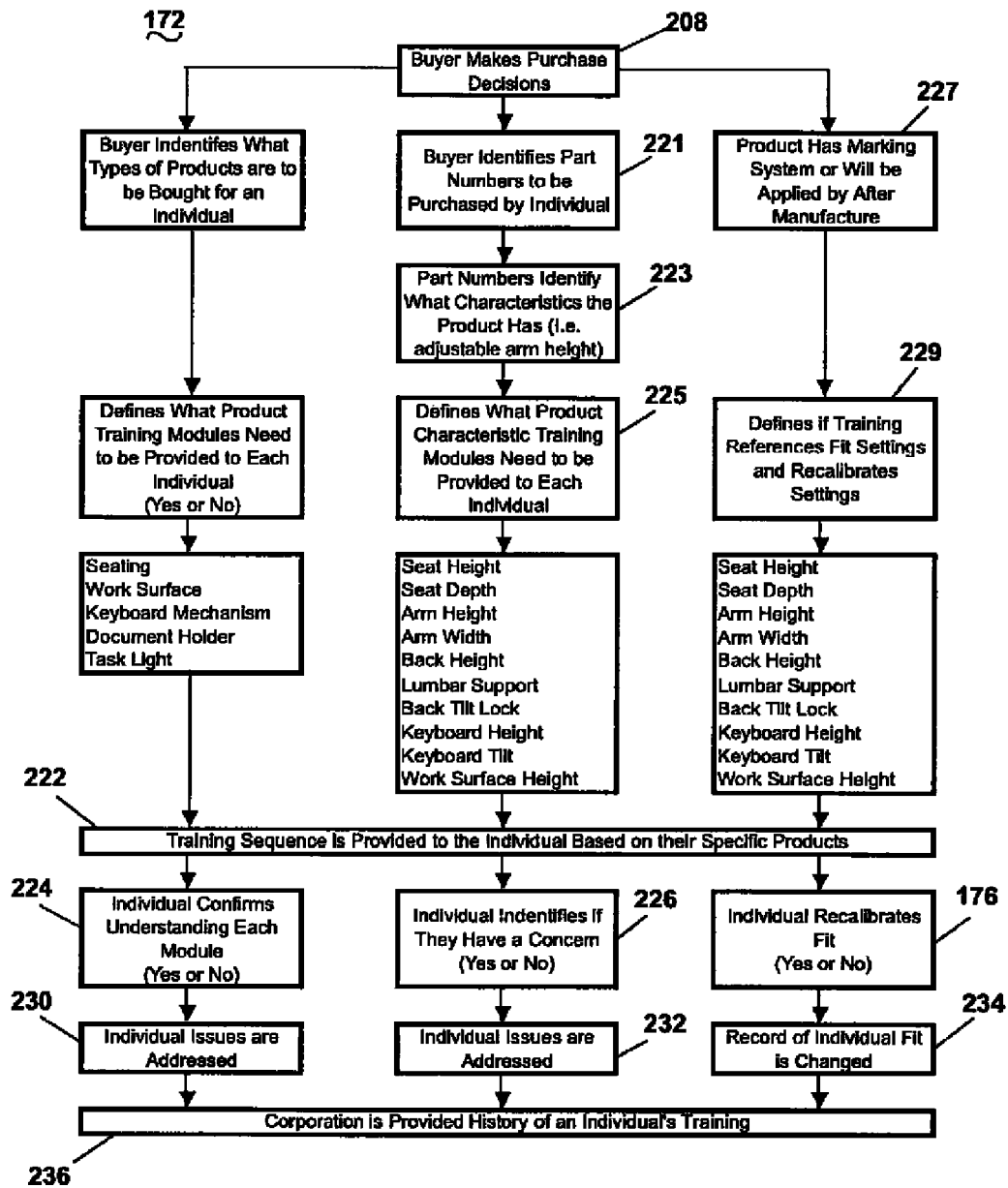
FIG. 11 is a schematic illustrating a training process as employed in the business method in FIG. 2.

After the fit settings are determined in step 168, they are correlated in step 170 to a marking system. One example of the marking system is shown in FIG. 9, wherein fit settings for various aspects of the workspace are assigned to a color. A label 58, such as an example color bar label 58 in FIG. 10, wherein a single color corresponds to a range of settings and each color is sub-graduated to differentiate between individual settings, can be applied to the appropriate area or areas of the workspace to provide a visual guide for the individual for adjusting furniture and other items in the workspace. The marking system in FIGS. 9 and 10 is exemplary, and the marking system utilized in the system and method 10 can vary significantly therefrom. It is within the scope of the invention to use other suitable marking systems that provide a visual indication of an individual's fit settings for various components of furniture or other items in the workspace. The marking system is preferably visually perceptible from a distance to allow for facile visual monitoring or auditing of the fit settings. For example, the seat height fitting for the above Asian male corresponds to blue; therefore, he can move the seat up or down accordingly so that the seat height is positioned in a blue range 59 of the label 58. An auditor should preferably be able to quickly, effortlessly, and visually confirm or disprove that the Asian male has aligned his seat height in the blue range 59 of the label 58.

The next step in the system and method 10 is to train 172 the organization or individual to ensure that the organization or individual is aware of how to utilize the furniture or accessories in the correct ergonomic manner as determined in the furniture fitting 168. After the purchasing decisions 208 are completed, the buyer determines 221 the product part number or numbers that correspond to an individual's product requirements. The part numbers identify 223 product characteristics, such as adjustable arm height, and help define 225 training modules that correspond to the characteristics. As a result, the training modules for an individual are efficiently customized to that individual's needs. Simultaneously, the buyer determines 227 if the product has a marking system or if a marking system will be applied after manufacture. Once the marking system is in place, the fit settings are compared 229 to the training references and are calibrated, if necessary. Next, the training modules are provided 222 to the individual based on the type of product or product part number. The modules contain step-by-step instructions that describe how to adjust the portions of the product that correspond to the identified part numbers. For example, a seat height adjustment instruction might direct the individual to rotate a knob located on the rear of the seatback counterclockwise until the seatback is positioned at the appropriate marker. The individual confirms 224 whether or not they understand each module, identifies 226 any concerns, and/or recalibrates 176 the fit if necessary. After individual issues are addressed 230, 232 and a record of the individual fit is changed 234, the organization is provided 236 a history of an individual's training.

Once the fitted furniture and other items in the workplace are in use, the system and method 10 can be utilized to monitor 178 the health and ergonomic risk of the organization or individual. Changes observed in the heath index or ergonomic risk can provide an early (i.e. prior to an injury) notification signal 180 that the risk level of the organization or individual needs to be reassessed. As discussed hereinafter, the monitoring aspect of the system and method 10 is a very useful tool for internal and external safety audits and for groups that protect workers' rights, such as labor unions.

As part of the monitoring aspect of the system and method 10, the organization can quantify the effects of implemented solutions for a task or workspace environment by determining changes in frequency of injury or changes in productivity. Obviously, changes in frequency of injury can be evaluated by comparing the number and frequency of injuries that occurred before and after the solutions were implemented. To evaluate changes in productivity, metrics, which can be determined either by survey or by physical performance testing, that assess productivity based on specific criteria can be imbedded into the system and method 10. For example, typing efficiency can be measured by the number of keystrokes an individual can correctly execute in a given period of time. This test can be performed prior to and following implemented solutions, and differences in the results can be used to quantify changes in productivity.

Figure 12:
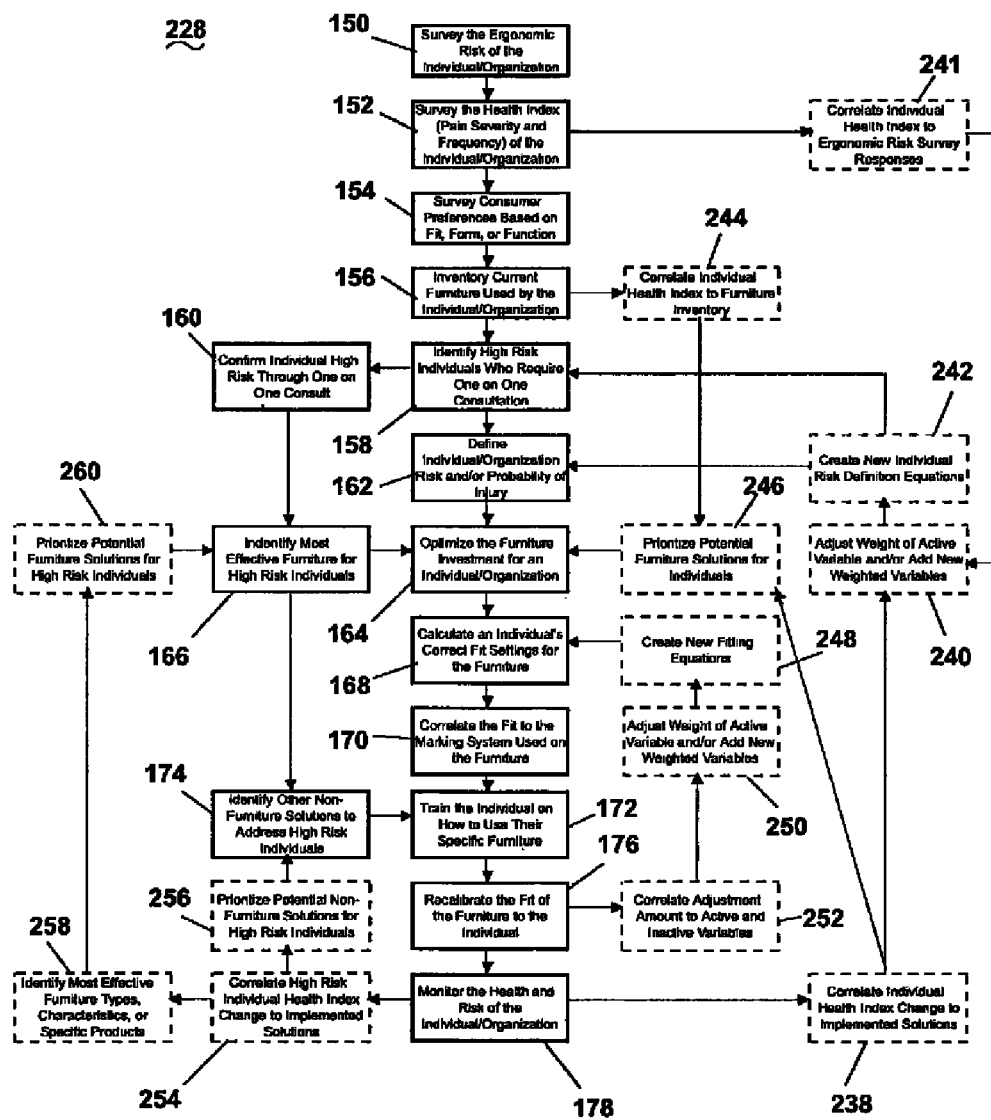
FIG. 12 is a schematic illustrating a continual improvement process that builds upon the business method shown in FIG. 2, wherein steps for the continual improvement process are shown with dashed borders.

The system and method 10 can be continually improved 228 with respect to risk assessment, solutions for high-risk individuals, furniture recommendations, and furniture fittings. Steps in the system and method 10 corresponding to continual improvement are shown with dashed borders in FIG. 12. As solutions are implemented in the workspace, historical data sets are established, and the equations and processes for identifying high-risk individuals, defining ergonomic risk, and fitting furniture can be modified and fine-tuned for greater prediction accuracy.

In the case of risk assessment, changes in the heath index of an individual can be correlated 238 to the implemented solutions. Based on the correlation results, the weight of active variables can be adjusted 240 and/or inactive variables can be weighted and added 240 to create 242 new risk equations for determining an organization or individual's ergonomic risk in steps 158 and 162. Additionally, active variables can be adjusted 240 or inactive variables can be added 240 as a result of correlating 241 initial individual health index survey results from step 152 with initial ergonomic risk survey results from step 150. The dynamic inclusion of inactive variables and the statistical weighting thereof ensures that the equations are continuously updated and accurate.

As part of continual improvement in solutions for high-risk individuals, changes in the heath index of a high-risk individual can be correlated 254 to the implemented solutions, and the correlation can be used to prioritize 256 potential non-furniture solutions for the high-risk individual. The prioritized non-furniture solutions can then assist in identifying potential non-furniture solutions for the high-risk individual in step 174.

In addition to non-furniture solutions, furniture recommendations for high-risk individuals can be continually improved. Correlation 254 of changes in the heath index of a high-risk individual to the implemented solutions can be used to identify 258 the most effective types and characteristics of furniture and specific products. This information can assist in prioritizing 260 potential furniture solutions for high-risk individuals, which can, in turn, help identify the most effective furniture for high-risk individuals in step 166.

Improvements in non-high-risk furniture recommendations are accomplished by combining correlations 238 between an individual's health index change and implemented solutions with correlations made in step 244 between the individual's initial heath index determined in step 152 and the inventory of current furniture from step 156 to prioritize 246 potential furniture solutions for individuals. The prioritized furniture solutions can be employed to optimize the furniture investment in step 164.

If the fit of the furniture for an individual is recalibrated in step 176, the adjustment amount can be correlated 252 to active and inactive variables as part of continual improvement for the furniture fitting process. Following correlation 252, the weight of active variables can be adjusted 250 and/or inactive variables can be weighted and added 250, similar to the dynamic inclusion of inactive variables and the statistical weighting thereof discussed above for the risk equations, to create new fitting equations in step 248. The new, improved fitting equations are then employed in step 168 to calculate an individual's fit settings.

An important outcome of the above described improvement processes is that equations, such as those that determine high risk individuals and furniture settings, used in the system and method 10 are continuously altered, added, deleted, or otherwise edited. The equations, which are determined from past experience and research, are inherently improved as the system and method 10 is implemented. As sample size increases, larger quantities of data are available for equation refinement.

Figure 13:
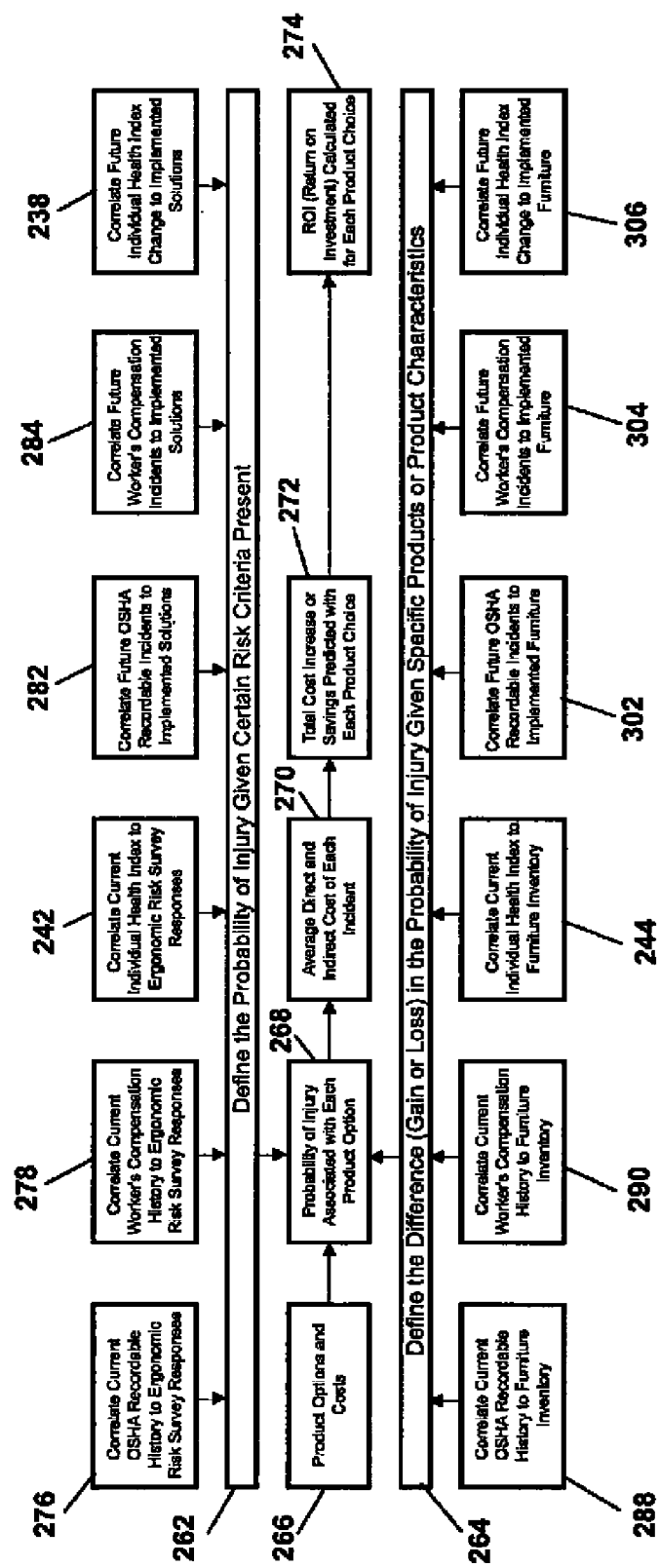
FIG. 13 is a schematic illustrating a Return on Investment calculation process as employed in the business method in FIG. 2.

A critical feature of the system and method 10 is the ability to calculate a Return on Investment metric 100. The ROI provides the buyer a basis for determining whether or not a purchase decision is cost-effective. The process for calculating the ROI is depicted schematically in FIG. 13. In general, product (furniture and other workspace items) options and cost 266, probability 268 of injury associated with each product option, average direct and indirect cost 270 of each injury incident, and total cost increase or savings 272 predicted for each product choice are simultaneously evaluated to compute 274 the ROI for each product choice.

The probability 268 of injury for a product option depends on several factors relating to the risk of injury and to specific products. As shown in the upper portion of FIG. 13, current Occupational Safety and Health Administration (OSHA) recordable history 276, current worker's compensation history 278, and current individual health index survey results 242 can be separately correlated to ergonomic risk survey responses from step 150, and future OSHA recordable incidents 282, future worker's compensation incidents 284, and future changes in an individual's health index 238 can be correlated with implemented solutions to define the probability 262 of injury for certain risk criteria. Referring now to the lower portion of FIG. 13, current OSHA recordable history 288, current worker's compensation history 290, and current individual health index survey results 244 can be separately correlated to furniture inventoried in step 156, and future OSHA recordable incidents 302, future worker's compensation incidents 304, and future changes in an individual's health index 306 can be correlated with implemented furniture to define any difference 264 in the probability of injury for specific products. Together, the probability 262 of injury for certain risk criteria and the difference 264 in the probability of injury for specific products determine the probability 268 of injury associated with each product option.

EXAMPLE

A Workplace Office Application

One application of the system and method 10 according to the invention will now be described with respect to a general office workplace and the ergonomic scenarios typically encountered by workers therein.

Figure 14:
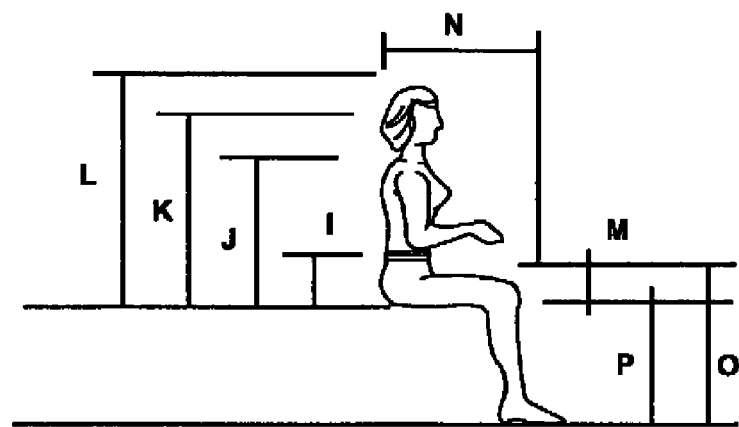
FIG. 14 is a side elevational view of a seated human form with sample dimensions making up a portion of the personal attributes for the method illustrated in FIG. 1.
Figure 15:
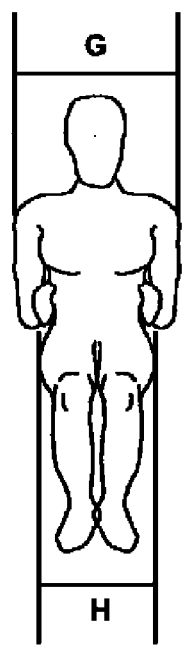
FIG. 15 is a front elevational view of a seated human form with additional sample dimensions making up a portion of the personal attributes for the method illustrated in FIG. 1.

A first step of this example relates to the collection, compilation and input of the personal attributes 14 of the workers in the office workplace. FIGS. 14-15 show a general human form with dimensions which can be helpful in determining the personal attributes 14 of each worker. Reference letters I-P can be found in FIG. 14 while reference letters G-H can be found in FIG. 15. These human form dimensions are summarized in the following table.

| Ref | Dimension | Definition |
|---|---|---|
| G | Shoulder Breadth | Horizontal distance between the lateral most aspects of the shoulder, measured with the subject sitting erect. |
| H | Hip Breadth | Horizontal distance between the lateral most aspects of the hip, measured with the subject sitting erect. |
| I | Elbow Resting Height | Vertical distance from the sitting surface to the bottom of the elbow measured with the subject sitting erect with the upper arm vertical at the side and the forearm at a right angle to the upper arm. |
| J | Shoulder Height | Vertical distance from the sitting surface to the lateral acromial process of the shoulder, measured with the subject in an erect sitting posture. |
| K | Eye Height | Vertical distance from the sitting surface to inner corner of the eye, measured with the subject sitting erect. |
| L | Sitting Height | Vertical distance from the sitting surface to the top of the head with the subject sitting erect. |
| M | Thigh Clearance | Vertical distance from the sitting surface to the top of the thigh at its maximum vertical height. Measurement is taken with the subject sitting erect. |
| N | Buttocks-Knee Length | Horizontal distance from the plane created at the posterior most aspect of the buttocks to the back of the knee, measured with the subject sitting erect. |
| O | Knee Height | Vertical distance from the floor to the upper aspect of the knee, measured with the subject sitting erect. |
| P | Stool Height (Popliteal Height) | Vertical height from the floor to the sitting surface measured with the subject sitting erect, with his/her knees and ankle positioned at 90 Å°. |

It will also be understood that the above human form dimensions are by example only, and any other information about the human form can make up the input data for the personal attributes without departing from the scope of this invention.

Other inputs/information which can be used for the personal attributes 14 can include, but are not limited to: standing height, weight, gender (male/female), age (e.g., generally noted by decade of life), ADA issue (yes/no), recent injury, shoulder (pain, numbness, weakness, loss of range of motion), elbow (pain, numbness, weakness, loss of range of motion), wrist/hand (pain, numbness, weakness, loss of range of motion), neck (pain, numbness, weakness, loss of range of motion), back (pain, numbness, weakness, loss of range of motion), lower extremity (hip, knee, ankle) (pain, numbness, weakness, loss of range of motion), etc.

Figure 16:
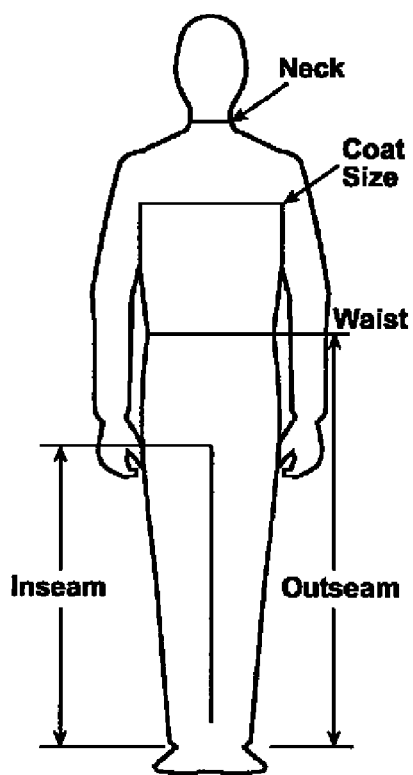
FIG. 16 is a front elevational view of a human form with additional sample dimensions making up a portion of the personal attributes for the method illustrated in FIG. 1, wherein the sample dimensions of FIG. 16 identify typical clothing sizes.
Figure 17:
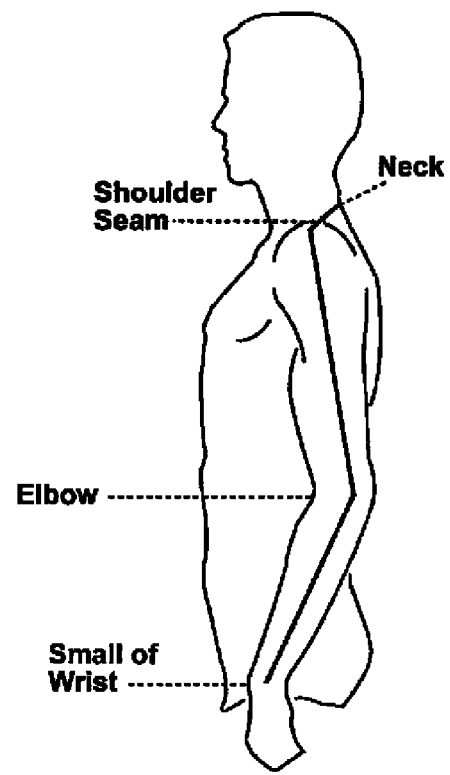
FIG. 17 is a side elevational view of a human form with additional sample dimensions making up a portion of the personal attributes for the method illustrated in FIG. 1, wherein the sample dimensions of FIG. 17 identify additional types of dimensions available from typical clothing sizes.
Figure 18:
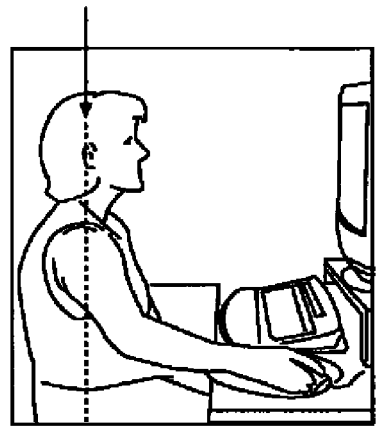
FIG. 18 is an example of a human form seated at a desk in a proper ergonomic position.
Figure 19:
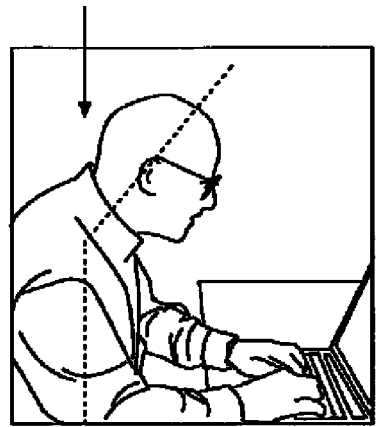
FIG. 19 is an example of a human form seated at a desk in a similar orientation as FIG. 18 but in an improper ergonomic position.
Figure 20:
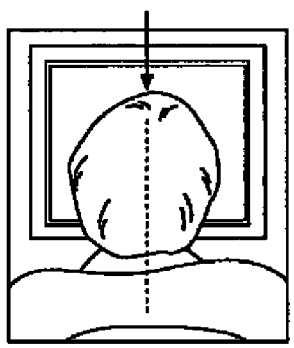
FIG. 20 is an example of a human form viewing a computer monitor in a proper ergonomic position.
Figure 21:
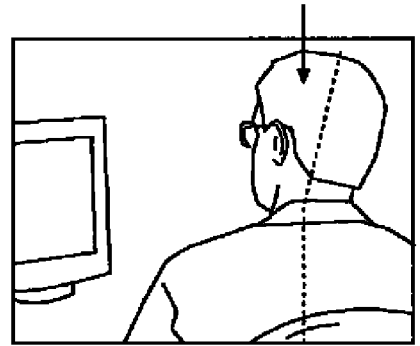
FIG. 21 is an example of a human form viewing a computer monitor in a similar orientation as FIG. 20 but in an improper ergonomic position.
Figure 22:
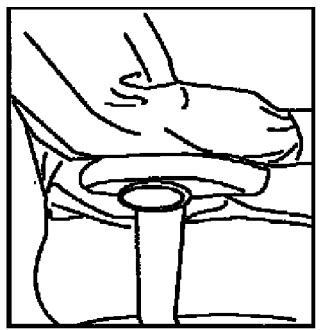
FIG. 22 shows a fragmentary portion of a human form seated on an office furniture chair with an armrest in a proper ergonomic position.
Figure 23:
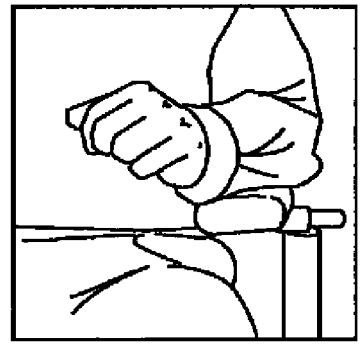
FIG. 23 shows a front elevational view of the human form of FIG. 22 with an armrest in a proper ergonomic position.
Figure 24:
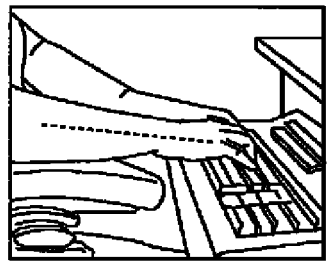
FIG. 24 is an example of a human form seated at a computer keyboard showing an arm and a wrist of the human form in a proper ergonomic position.
Figure 25:
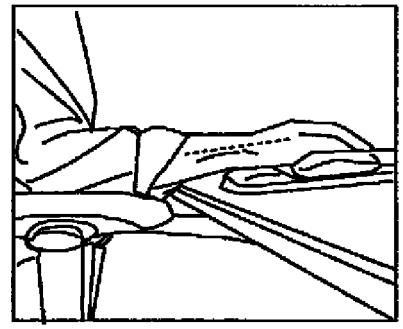
FIG. 25 is an example of a human form seated at a computer keyboard in a similar orientation as FIG. 24 but showing the arm and the wrist of the human form in an improper ergonomic position.
Figure 26:
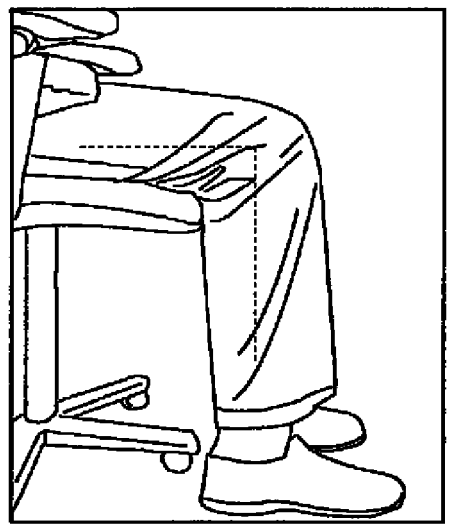
FIG. 26 is an example of a human form seated in an office furniture chair showing legs of the human form in a proper ergonomic position.
Figure 27:
FIG. 27 is an example of a human form seated in an office furniture chair in a similar orientation as FIG. 26 showing feet of the human form in a proper ergonomic position with respect to the floor.
Figure 31:
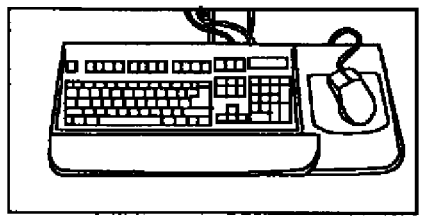
FIG. 31 shows a tray adapted to support both a computer keyboard and a pointing device, such as a mouse, as it has been found that a sufficiently large keyboard and mouse tray provides better ergonomic support than with the keyboard and mouse supported at different levels or on different supports.
Figure 32:
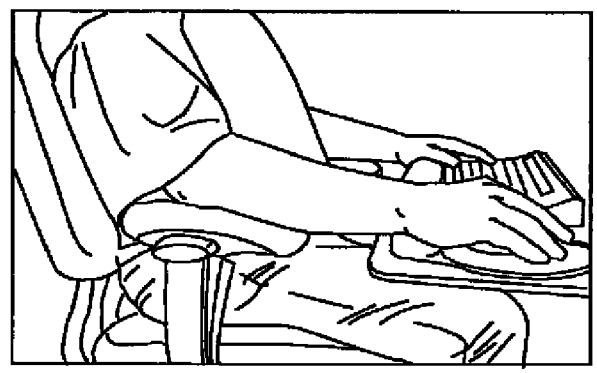
FIG. 32 is an example of a human form seated at a computer keyboard with a pointing device located directly adjacent to the keyboard, wherein the keyboard and the pointing device are supported on a common keyboard tray, wherein the keyboard tray provides a proper ergonomic position so that the human form does not need to extend its arms to reach the keyboard and the pointing device.
Figure 33:
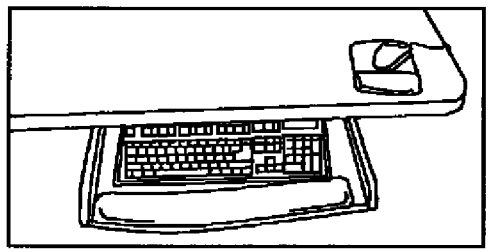
FIG. 33 shows an example of a keyboard and a pointing device, such as a mouse, supported at different levels at a user workstation, thus providing an improper ergonomic position.
Figure 34:
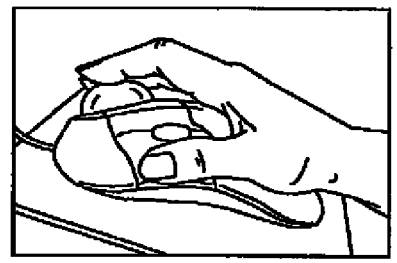
FIG. 34 shows an example of a hand of a human form placed on a pointing device which fits the hand of the human form, thus providing a proper ergonomic position.
Figure 35:
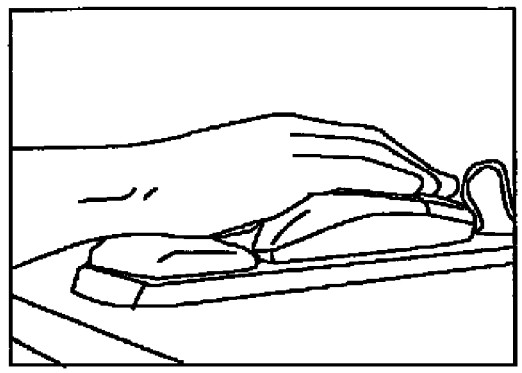
FIG. 35 shows an example of a hand of a human form in which a wrist of the human form is resting on a support so that the wrist and hand of the human form do not rest on sharp or hard edges, thus providing a proper ergonomic position.

It is also a feature of this invention that the compilation and collection of the personal attributes 14 of the workers can be done in a streamlined fashion by a unique method as described herein. Instead of performing physical measurements of the workers as contemplated by the description of FIGS. 14-15, sizes of clothing worn by the workers can be collected by a simple survey of the workers and the dimensions G-P shown in FIGS. 14-15 can be calculated by known methods. Examples of dimensions available from clothing sizes are shown in FIGS. 16-17, although other clothing sizes are available and can provide additional dimensional information for compiling the personal attributes 14 of the workers. Correlation of the dimensions of FIGS. 14-15 to the clothing sizes shown in FIGS. 16-17 is illustrated in the following table.

| Ref | Dimension | Correlation to Clothing Size |
|---|---|---|
| I | Elbow Resting Height | fn (P) + fn (standing height) |
| J | Shoulder Height | fn (P) + fn (standing height) |
| K | Eye Height | fn (P) + fn (standing height) |

-continued

| Ref | Dimension | Correlation to Clothing Size |
|---|---|---|
| L | Sitting Height | fn (P) + fn (standing height) |
| M | Thigh Clearance | fn (P) + fn (body weight) |
| N | Buttocks-Knee Length | fn (inseam length) |
| O | Knee Height | fn (inseam length) |
| P | Stool Height (Popliteal Height) | fn (inseam length) |
| G | Shoulder Breadth | fn (coat size) |
| H | Hip Breadth | fn (waist measurement of slacks for males or dress size for women) |

It will be understood that the convention "fn (P)" is used to describe that an input is a "function" of dimension "P".

Using the clothing sizes and other key data supplied by the workers can be used to relate them to historical anthropometric information to determine a correlation rate. This solution can often be more predictive, simpler, and cheaper to implement. It is also contemplated that the personal attributes 14 can be made up of a combination of rote physical measurements and clothing sizes, i.e., the two methods of collection of the personal attributes 14 are not mutually exclusive.

Examples of environmental attributes 18 will now be described with respect to FIGS. 18-47. The following describes an input stage of the system/method 10 according to the invention in which a worker's environment can be described. The environmental attributes 18 can be provided via a survey, a touch screen kiosk, a web-based form, and the like. The environmental attributes 18 are divided for purposes of convenience and understanding into six sections: (1) worker positioning; (2) chair configuration; (3) keyboard and input device positioning, (4) monitor positioning; (5) leg positioning; and (6) accessory positioning.

First, the work environment is preferably designed or arranged to provide optimal positioning while performing computer-related tasks.

A worker's head and neck are preferably upright (not bent down or rearwardly). A worker can select whether the workplace environment positions the worker's head: (1) in a proper ergonomic position in which the worker's head and neck are upright (see FIG. 18); (2) in an improper ergonomic position in which the worker's head and neck are bent downwardly (i.e., flexed as in FIG. 19) or upwardly (i.e., extended).

A worker's head, neck and trunk are preferably faced forward (not rotated): A worker can select whether the workplace environment positions the worker's head, neck and/or trunk: (1) in a face forward proper ergonomic position (see FIG. 20); or (2) in a rotated improper ergonomic position (see FIG. 21).

A worker's shoulders and upper arms are preferably generally perpendicular to a floor (not stretched forward) and relaxed (not elevated or hunched). A worker can select whether the workplace environment positions the worker's shoulder and arms: (1) generally perpendicular to the floor in a proper ergonomic position (see, e.g., FIG. 22); or (2) in an improper ergonomic position where the worker's shoulder and arms are stretched forward and/or elevated.

A worker's upper arms and elbows are preferably close to the body (not extended outward). A worker can select whether the workplace environment positions the worker's upper arms and elbows: (1) close to the body in a proper ergonomic position (see FIG. 23); or (2) extended outwardly in tension in an improper ergonomic position.

A worker's wrist and hands are preferably straight (not bent up or down and/or sideways toward the worker's little finger). A worker can select whether the workplace environment positions the worker's wrists and hands: (1) in a straight proper ergonomic position (see FIGS. 24 and 25); or (2) in an improper ergonomic position where the worker's wrists and hands are bent up or down (extended or flexed) and/or deviated toward the little-finger side (ulnar deviation).

A worker's thighs are preferably positioned about parallel to the floor and the worker's lower legs are preferably positioned generally perpendicular to the floor. A worker can select whether the workplace environment positions the worker's: (1) thighs parallel to the floor and lower legs perpendicular to the floor in a proper ergonomic position (see, e.g., FIG. 26); or (2) thighs not parallel and/or the lower legs not perpendicular to the floor in an improper ergonomic position.

A worker's feet preferably rest flat on the floor or are supported by a stable footrest. A worker can select whether the workplace environment positions the worker's feet: (1) flat on the floor or on a stable footrest in a proper ergonomic position (see FIG. 27); or (2) askance on the floor or are on an unsupported or a poorly-supported footrest in an improper ergonomic position.

Second, an office furniture chair should be designed to provide optimal positioning while performing computer related tasks. The worker can also select environmental attributes 18 relating to the positioning of a seating member.

A chair backrest preferably provides support for the worker's lower back. A worker can select whether the workplace environment positions the worker's chair: (1) in a proper position of the chair backrest locating the backrest in a proper ergonomic position (see FIG. 28); or (2) the chair backrest is too high or too low, positioning the worker in an improper ergonomic position.

A chair should have a sufficient width and depth to accommodate the worker (i.e., the seat pan is not too big or too small). A worker can select whether the worker's chair: (1) has proper parameters of the seatpan seating the worker in a proper ergonomic position; or (2) the seatpan width is too wide or narrow or the seatpan depth is too long or too short.

Preferably, a front edge of the seat does not press against the back of the knee or lower leg of the worker. A worker can select whether the worker's chair: (1) has proper positioning of front edge of the seat so that the front edge does not touch the worker's leg (see FIG. 29); or (2) the front edge of seat presses on the rear side of the knee/lower leg of the worker, creating an undesirable ergonomic condition.

The chair also preferably has cushioning and is rounded (i.e., has a waterfall-type or cascading front edge to the seat). A worker can select whether the worker's chair: (1) is a cushioned seat with a waterfall edge providing a proper ergonomic seating surface; or (2) has a seat without cushioning and/or a seat without a waterfall edge providing an improper ergonomic seating surface.

A chair should also have armrests that support both forearms while the worker is seated therein. The armrests should not interfere with the worker's body movement. A worker can select whether the worker's chair: (1) has proper forearm support while performing computing tasks thus providing a proper ergonomic position (FIG. 30); or (2) has improperly supported forearms and/or a seat configuration wherein the worker's lower legs are not supported in a perpendicular fashion.

Third, any keyboard and/or input device (such as a pointing device like a mouse or trackball) should be arranged to provide optimal positioning while performing computer-related tasks.

A support tray for the keyboard/input device should preferably be stable and sufficiently large to hold both the keyboard and the input device on the same planar surface. A worker can select whether the workplace environment has a keyboard tray in which: (1) the keyboard platform/tray allows placement of both the keyboard tray and input device thereon in a common planar arrangement, thus delivering a proper ergonomic position (see FIG. 31); or (2) the keyboard platform/tray does not allow placement of both items thereon leaving the keyboard and pointing device in an improper ergonomic position.

The input device (e.g., a mouse or a trackball) is preferably located directly adjacent to the keyboard so it can be operated without requiring the worker to reach for it. A worker can select whether the workplace environment positions the input device: (1) directly adjacent to the keyboard, thus providing a desirable ergonomic position (see FIG. 32); or (2) the position of the input device requires the worker to reach for it during operation (see FIG. 33).

The shape and/or size of the input device preferably fits the hand of the worker (i.e., not too big or small). A worker can select whether the input device: (1) is properly sized for the worker's hand and finger movement (see FIG. 34); or (2) the input device is either too small or too large for the user.

Preferably, the worker's wrist and hands do not rest on sharp or hard edges. A worker can select whether the workplace environment: (1) properly positions the worker's wrist and hand providing a desirable ergonomic environment (see FIG. 35); or (2) the worker's wrist and/or hand are positioned over a sharp, hard or otherwise uncomfortable edge creating an improper ergonomic condition.

Fourth, the computer monitor is preferably arranged to provide optimal positioning while performing computer related tasks. For example, a top edge of the monitor screen is preferably at or below eye level so the worker does not have to bend his or her head and/or neck up or down (i.e., cervical flexion or extension). A worker can select whether the workplace environment has a monitor which: (1) is properly positioned in a desirable ergonomic position (see FIG. 36 for non-bifocal/trifocal wearers and FIG. 37 for bifocal/trifocal wearers); or (2) has the top edge of the monitor positioned too high or too low. Bifocal and/or trifocal wearers are preferably able to read the screen without bending the worker's head/neck up or down this situation is illustrated in FIG. 37 where the glasses-wearer positions the monitor at a downwardly-angled position to accommodate the line of sight required by the bifocals/trifocals. A worker can select whether the workplace environment has: (1) a properly positioned monitor for desirable ergonomic line of sight purposes (as in FIGS. 36-37); or (2) the monitor is positioned too high or too low.

The distance from the worker to the monitor is preferably arranged so that the worker can read the monitor screen without leaning the worker's head, neck or trunk forwardly or rearwardly. A worker can select whether the workplace environment has: (1) an ergonomically-positioned monitor distance (see the arm's-length example in FIG. 38); or (2) a monitor reading distance that is too far or too near.

The monitor is also preferably positioned directly in front of the worker (with no twisting or rotation of the worker's head or trunk). A worker can select whether the workplace environment has: (1) a properly ergonomically-positioned monitor angular position with respect to the worker's head/trunk (see FIG. 39); or (2) the monitor position is off to the side requiring the worker to rotate the worker's head/trunk to view the monitor (see FIG. 40).

Preferably, no glare is imparted to the monitor screen by ambient lighting in the workplace environment that would require a worker to assume an awkward posture or position to read the screen. A worker can select whether the workplace environment has: (1) a monitor with no glare; or (2) monitor with glare (see the glare-filled monitor screen in FIG. 41).

Fifth, the work area is preferably designed to provide optimal positioning while performing computer related tasks. For example, a worker's thighs preferably have appropriate clearance between the chair and a computer work-surface/keyboard tray so that the user's thighs are not trapped between the chair and the work-surface/keyboard tray. A worker can select whether the workplace environment has: (1) appropriate thigh clearance between the chair and the computer work-surface/keyboard tray providing a desirable ergonomic condition; or (2) the worker's thighs are trapped between the chair and the computer work-surface/keyboard tray creating an improper ergonomic position.

In addition, the worker's legs and feet preferably have appropriate clearance under the computer table so that the worker can get close enough to the keyboard/input device for comfortable operation thereof. A worker can select whether the workplace environment has: (1) appropriate leg and foot clearance under the work-surface, creating a proper ergonomic condition; or (2) the worker encounters some sort of barrier under the computer table which does not allow the worker to get sufficiently close to the keyboard or input device for comfortable operation and, thus, an improper ergonomic condition.

Sixth, the work area is preferably designed to provide optimal positioning of computer-related accessories when they are deemed appropriate for use. For example, a document holder (if provided) is stable and large enough to hold documents that are used (perhaps for transcription or editing). A worker can select whether the workplace environment has: (1) an appropriately-sized document holder for medium to large documents (see FIG. 42); or (2) a poorly-sized document holder for a given set of task requirements.

In addition, the document holder (if provided) is preferably placed at about the same height and distance as the monitor screen. This will minimize the worker's head movement when the worker looks between the document on the document holder and the monitor screen. A worker can select whether the workplace environment has: (1) a properly-positioned document holder creating a desirable ergonomic position (see FIG. 42); or (2) a document holder positioned off to the side requiring a turn of the head to view in an improper ergonomic position (see FIG. 43 for an example).

If provided, a worker's wrist rest is preferably padded and free of sharp edges. A worker can select whether the workplace environment has: (1) a padded wrist rest that is free from sharp edges creating a desirable ergonomic condition (see FIGS. 44-45); or (2) has a wrist rest that demonstrates a sharp edge and/or lacks padding, creating an improper ergonomic condition.

In addition, the wrist rest (if provided) allows the worker to keep its forearms, wrist and hands in a straight/neutral posture while utilizing the keyboard/input device. A worker can select whether the workplace environment has: (1) a properly-positioned wrist rest creating a proper ergonomic situation (see FIGS. 44-45); or (2) has a wrist rest position which requires excessive wrist flexion and/or extension.

Telephones are often used in the work environment. Preferably, the telephone can be used with the worker's head in an upright/neutral posture. In addition, the worker's shoulders are relaxed if the user chooses to perform computer tasks and phone tasks at the same time. A worker can select whether the workplace environment has: (1) proper phone postures during telephonic use (see FIG. 46 with a telephone headset shown as an example of proper ergonomic positioning); or (2) a deviated neck and/or shoulder posture while utilizing the telephone and/or the computer creating an undesirable ergonomic condition (see FIG. 47).

An example survey used to collect task-related attributes 16 is shown in FIG. 48. The questions shown in the example survey gather data regarding the duration and types of tasks performed in the work environment.

Once the personal, task and environmental attributes 14, 16 and 18, respectively, have been collected, they are supplied as inputs to the coding equation 12 to produce the output 20 as shown in FIG. 1.

The coding equation 12 is further described in the following paragraphs.

A function of the personal attributes 14 is described as:

$P=fn$(anthropometric data)(height)(weight)(gender)(age)(injury history)(etc.)

A function of the task attributes 16 is described as:

$T=fn$(length of workday)(% of workday spent computing)(hours of home computing)(type of software application)(type of computer, i.e., desktop, laptop, hand-held)

A function of the environmental attributes 18 is described as:

$E=fn$(working conditions)(seating interface)(keyboard/mouse interface)(monitor interface)(work area interface)(interface with computer accessories)(etc.)

The above functions are shown as examples as the inventors realize that many other mathematical calculations could be employed without departing from the scope of this invention.

Then, the risk of injury can be determined by:

Risk of injury=$fn(P·E·T)$ and the effect on office productivity can also be determined by Productivity Metric=$fn(P·E·T)$.

The following paragraphs outline some sample calculations and describe one example of the coding equation 12 in greater detail. A scoring procedure is introduced which places point values on each of the personal, task and environmental attributes 14-18 described by example above.

For example, with respect to the environmental attributes 18 described above, each negative answer to the ergonomic environmental characteristics described with respect to FIGS. 18-47 can be scored with a predetermined number of points (i.e., the more negative the ratings, the higher the effect on the risk of injury calculation). For example, the user positioning negative answers (section 1 above) could be scored as two points and the remaining sections 2-6 could be scored as one point. The total environmental attribute score can be determined by the sum of the negative answers, weighted according to that set forth above.

Office Environment Score($A$)=$A$ pts.

One simple example scoring of the personal attributes 14 can be done by scoring each of the measured criteria. The following table shows a sample table for the age personal attribute.

| Age | Female | Male |
|---|---|---|
| 20-35 | 3 | 1 |
| 35-50 | 4 | 3 |
| 50-65 | 2 | 2 |

Another sample criteria would be to add one point to the age tables above if the worker had a history of recent injury within a previous predetermined number of months, such as in the last quarter or last six months.

These same scoring techniques can be repeated for each of the personal attributes 14 collected.

Personal Demographics Score($B$)=$B$ pts.

Figure 36:
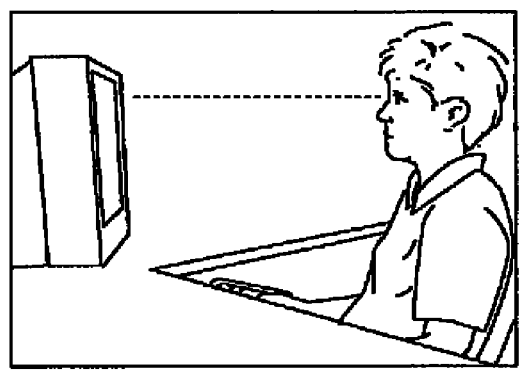
FIG. 36 shows a human form seated at a computer workstation illustrating a proper seating position for viewing a computer monitor thereof for non-bifocal/trifocal-wearing users.
Figure 37:
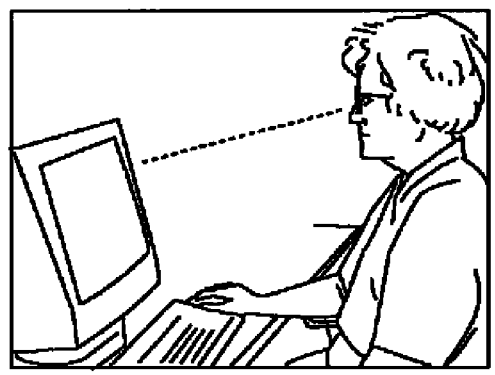
FIG. 37 shows a human form seated at a computer workstation illustrating a proper seating position for viewing a computer monitor thereof for bifocal/trifocal-wearing users.
Figure 38:
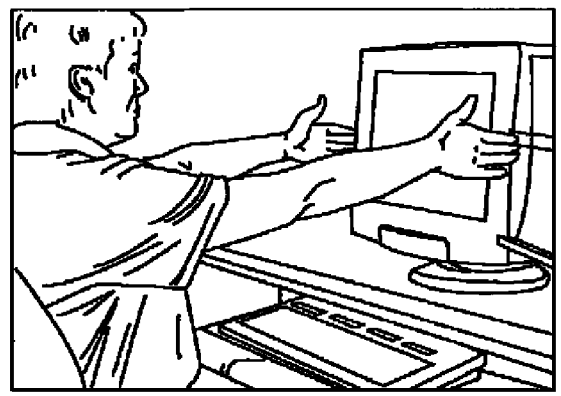
FIG. 38 shows a human form seated at a computer workstation illustrating a proper seating position for viewing a computer monitor at a proper ergonomic distance.
Figure 39:
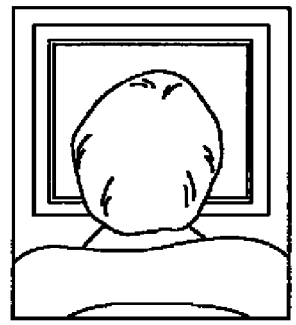
FIG. 39 shows a human form seated at a computer workstation showing a monitor position directly in front of the human form illustrating a proper ergonomic position.
Figure 40:
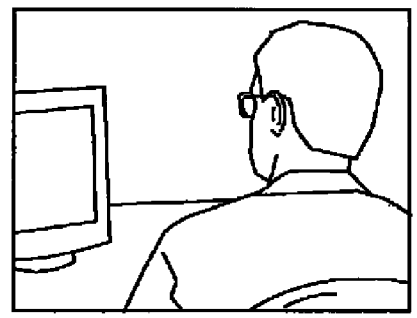
FIG. 40 shows a human form seated at a computer workstation showing a monitor positioned at an angle with respect to the human form showing an improper ergonomic position.
Figure 41:
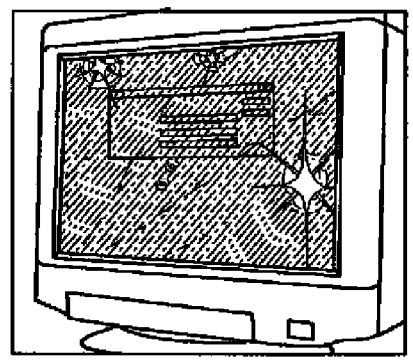
FIG. 41 shows a monitor for a computer workstation having an unacceptable level of glare imparted to the monitor by the ambient lighting surrounding the computer workstation thus illustrating an improper ergonomic situation.
Figure 42:
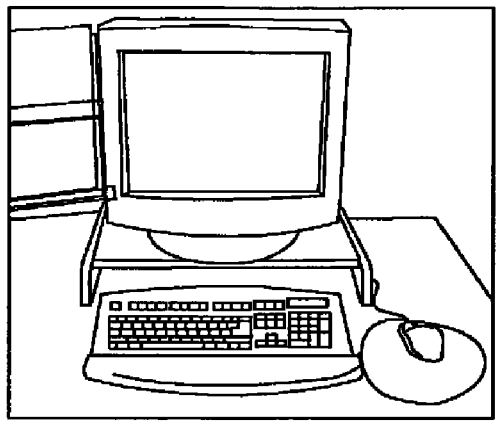
FIG. 42 shows a computer workstation having a document holder attached to a monitor providing a proper ergonomic position for a user seated at the workstation.
Figure 43:
FIG. 43 shows a human form seated at a computer workstation without a document holder requiring the user to twist his or her trunk and hold his or her head at an angle to read documents located adjacent to the workstation providing an improper ergonomic position.
Figure 44:
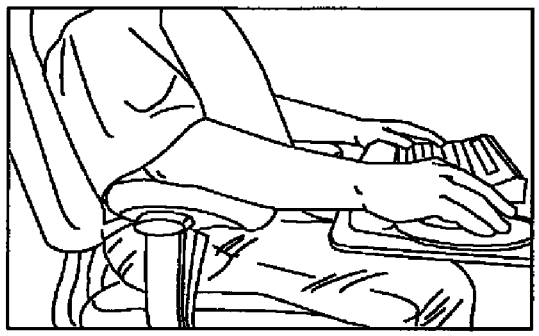
FIG. 44 shows a human form seated at a computer workstation including a keyboard and a pointing device with a wrist rest thereon allowing the hand of the human form to be kept in a neutral posture while using the keyboard and pointing device thus providing a proper ergonomic position.
Figure 45:
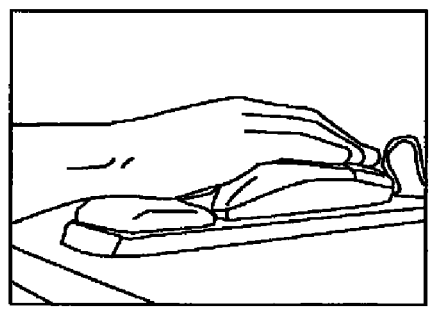
FIG. 45 shows the wrist rest and pointing device of FIG. 44 in greater detail.
Figure 46:
FIG. 46 shows a human form seated at a workstation using a telephone with the head in an upright/neutral posture permitting a proper ergonomic position.
Figure 47:
FIG. 47 shows a human form seated at a workstation using a telephone with the head in a deviated neck posture thus providing an improper ergonomic position.

In the event the sample survey (or something similar) shown in FIG. 36 is employed, the task attributes can be scored in similar fashion. The task attribute inputs are measured as a function of the average total time of computing each day (in the office example). The following table provides a sample criteria for scoring of one of the task attributes 16 shown in the survey of FIG. 36.

| Average of Daily Computing Time | Score |
|---|---|
| <1 hour computing time | 0.5 |
| 1-4 hours computing time | 1.0 |
| 4-7 hours of computing time | 2.0 |
| >7 hours of computing time | 4.0 |

The task attribute 16 score can then be calculated.

Office Related Task Score($C$)=$C$ pts.

A risk rating can be calculated within the coding equation 12 by the sample formula below:

Relative Risk Rating=$(A)·(B)·(C)$

Then, if an ordinal rating of the risk is desired, the numerical output of the risk rating calculation can be stratified in a categorized rating system. For example, if the risk rating were calculated on an 80-point scale (i.e., the highest possible score output by the coding equation 12 for rating risk is 80), the calculation for each worker could be categorized as follows.

| Total Score | 0-15 | 16-30 | 31-45 | 46-60 | Over 60 |
|---|---|---|---|---|---|
| RelativeRisk | Minimal | Low | Moderate | High | Very High |

Fictional Case Studies

The following section sets forth two case studies and provides the output 20 of the coding equation 12 as set forth above in the immediately preceding paragraphs. The first case study is a 43-year-old female with no history of injury and the second is a 45-year-old male with no history of injury. The various negative ergonomic features of each of their personal, task and environmental attributes 14-18 are provided below.

Case Study 1—43-Year-Old Female

The first case study environmental attributes 18 are:

| Section | Environmental Attribute | Score |
|---|---|---|
| 1 | Shoulders and upper arms are stretched forward | 2 |
| 2 | No armrest | 1 |
| 3 | Wrist and hands rest on sharp edge | 1 |
| 4 | Monitor is too high | 1 |
| | Environmental Attribute Score (A) | 5 pts |

The first case study personal attributes 14 (a simplified list of attributes is used for purposes of simplicity and illustration) are:

| Personal Attribute | Score |
| --- | --- |
| 43-year-old female | 4 |
| No recent history of injury | 0 |
| Personal Attribute Score (B) | 4 pts |

The first case study task attributes 16 (again, a simplified list of attributes is used for purposes of simplicity and illustration) are:

| Task Attribute | Score |
| --- | --- |
| Average of Daily Computing Time = 1-4 hours | 1 |
| Task Attribute Score (C) | 1 pt |

Then, the relative risk rating (using the stratified table of rating categories listed above in the sample 80-point sacle) can be calculated as:

Relative Risk Rating=$(A)\cdot(B)\cdot(C)=(5)\cdot(4)\cdot(1)=$20="Low Risk"

Case Study 2—45-Year-Old Male

The second case study environmental attributes 18 are:

| Section | Environmental Attribute | Score |
| --- | --- | --- |
| 1 | Head is not upright | 2 |
| 1 | Ulnar deviation | 2 |
| 2 | No armrest | 1 |
| 3 | Wrist and hands rest on sharp edge | 1 |
| 4 | Monitor is too low | 1 |
|   | Environmental Attribute Score (A) | 7 pts |

The second case study personal attributes 14 (a simplified list of attributes is used for purposes of simplicity and illustration) are:

| Personal Attribute | Score |
| --- | --- |
| 45-year-old male | 3 |
| No recent history of injury | 0 |
| Personal Attribute Score (B) | 3 pts |

The second case study attributes 16 (again, a simplified list of attributes is used for purposes of simplicity and illustration) are:

| Task Attribute | Score |
| --- | --- |
| Average of Daily Computing Time = 4-7 hours | 2 |
| Task Attribute Score (C) | 2 pts |

Then, the relative risk rating (using the stratified table of rating categories listed above in the sample 80-point scale) can be calculated as:

Relative Risk Rating=$(A)\cdot(B)\cdot(C)=(7)\cdot(3)\cdot(2)=$42="Moderate Risk"

As can be seen, each individual in a workplace can have these calculations performed, and a company can determine which individuals have more potential for injury than others.

The system and method 10 described herein provides an integrated sales and product promotion process, which requires the involvement of the entire distribution chain, from product development through training and audit process of the end user. A common language is utilized (i.e., measurement techniques) and processes for each person involved. For sellers of office products, their knowledge base is improved and the dealers have options of a more sophisticated selling process, which capitalizes the benefit of reducing workplace risk and injury. The sellers can also have the opportunity to sell new discrete products to an installed customer base, based on reduced risk (i.e., the output 20 of the coding equation 12 shown by example herein).

The system and method 10 set forth herein provides a user-friendly, fully integrated and systematic approach to measure the attributes of the person, the task, and the environment, and identifies optimal outcomes and related risk of injury and productivity improvement. The entire distribution chain can be involved in this process. The productivity of organizations can be improved by reducing lost workdays and worker injury. As will be described, a user of the system and method 10 is provided with the ability to assure appropriate installation and future compliance to safe work methods.

The system and method 10 can be used by sellers of products and managers of facilities to assess and manage workplace ergonomics. The user inputs information about a company's individual users, or groups of users (those who share a workstation), and tasks to be completed. Use of the system and method 10 can provide the user with a list of product options, risk rating, cost, calculated risk of injury, and productivity improvement estimates. The user can make buying decisions for furniture and equipment based on that information.

Furniture can be coded with a user-friendly and easily identifiable system (e.g., color-coded) to define different settings available for the product. The system and method 10 can provide a code by individual or groups of users, defining the settings the individual pieces of furniture must be set to, to support the decision criteria used by the buyer.

Turning to the example codings shown in FIGS. 49-61, an office chair 40 is shown comprising a seat 42 and a base 44 adjustably connected to the base by a seat height adjuster 46. A seatback 48 is also provided which is adjustably mounted to the seat 42 by a seatback height adjuster 50. The seat 42 has a pair of armrests 52 mounted thereto which are adjustably mounted in the vertical direction to the seat 42 by an armrest height adjuster 54 as well as in the lateral direction by an armrest lateral adjuster 56.

Figure 49:
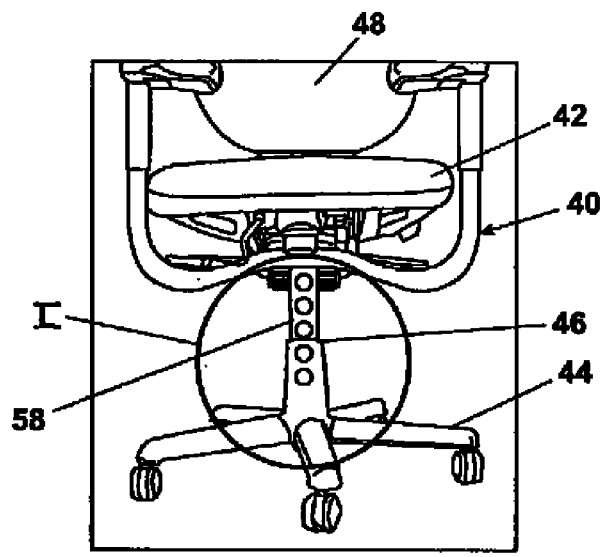
FIG. 49 illustrates an office chair provided with an ergonomic marking system according to the invention, the example shown in FIG. 49 being related to a seat height adjustment for the office chair.
Figure 50:
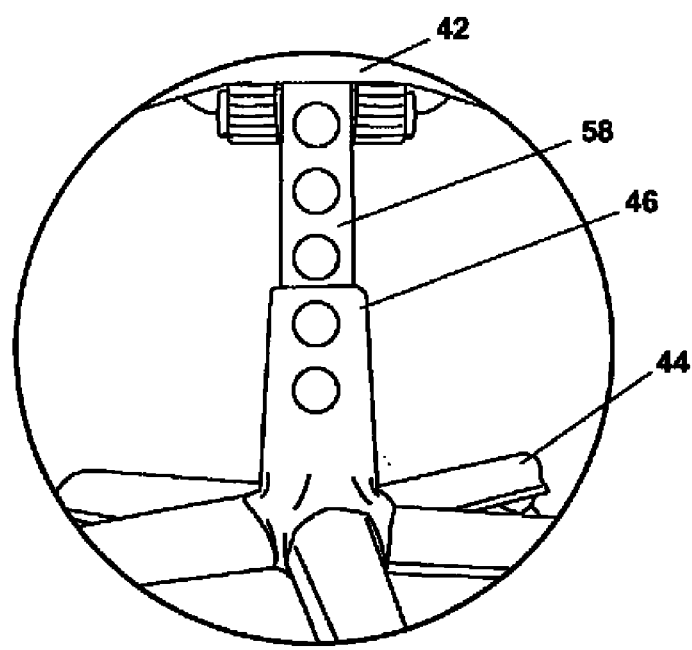
FIG. 50 is an enlarged elevational view of the region marked L in FIG. 49.
Figure 57:
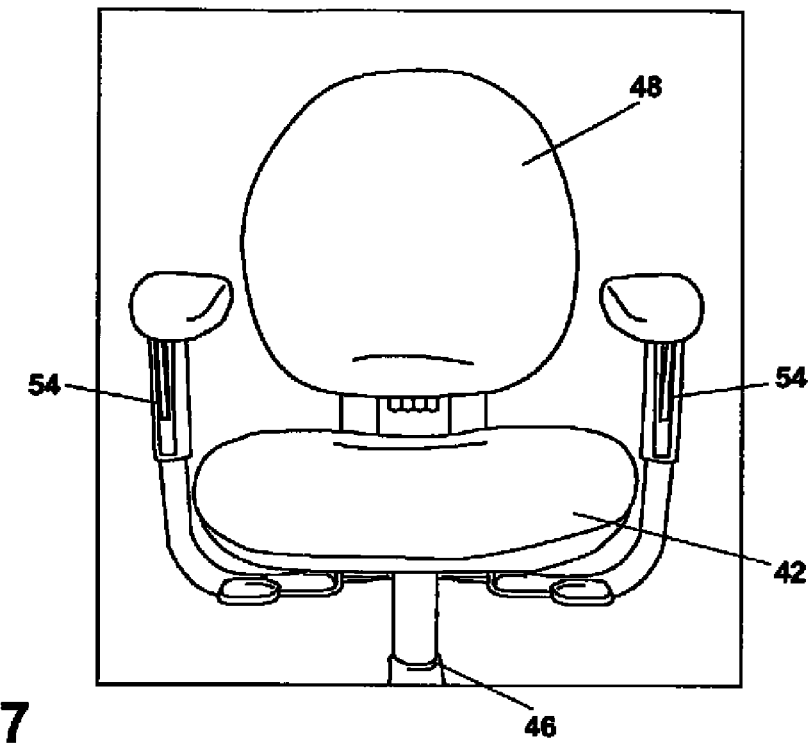
FIG. 57 illustrates an office chair provided with an ergonomic marking system according to the invention, the example shown in FIG. 57 being related to a lateral adjustment for an armrest of the office chair, the armrest lateral adjustment being shown in an outer position wherein only a portion of the ergonomic marking is shown in FIG. 57.
Figure 58:
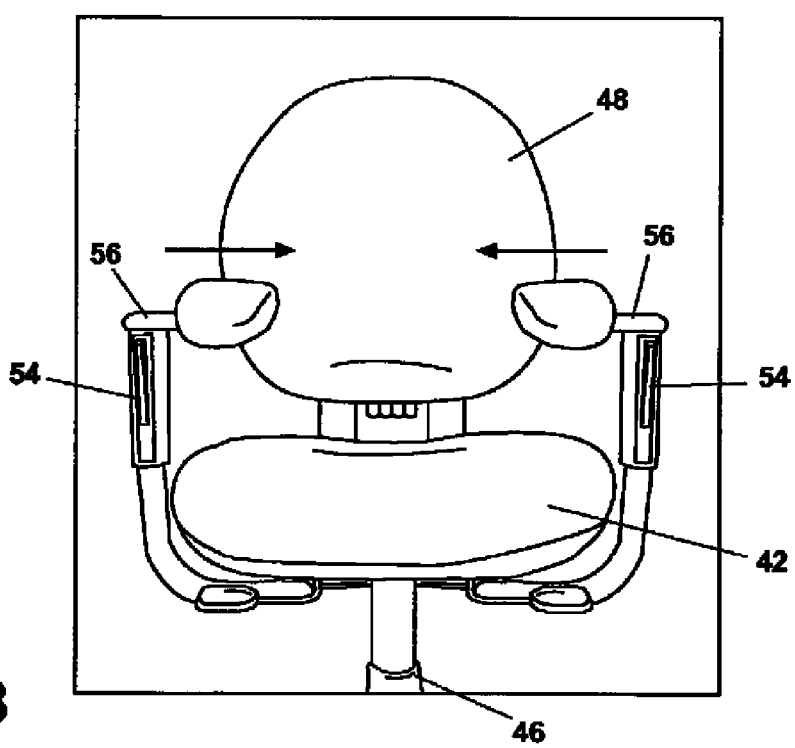
FIG. 58 illustrates the office chair of FIG. 57, wherein the lateral armrest position being shown in FIG. 58 is in an interposition, wherein a greater portion of the ergonomic marking is shown in FIG. 58.
Figure 59:
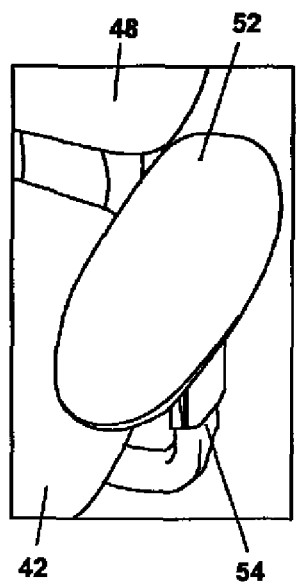
FIG. 59 shows the office chair of FIG. 57 with the armrest in a first lateral position.
Figure 60:
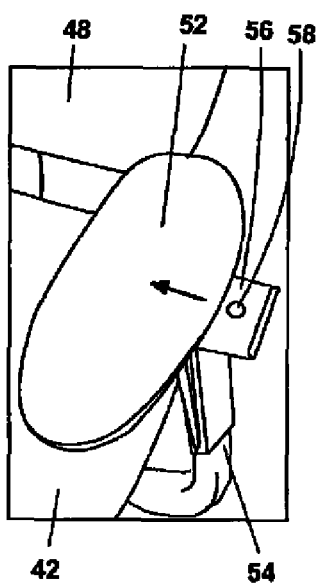
FIG. 60 shows the office chair of FIG. 57 with the armrest in a second lateral position, wherein a portion of the ergonomic marking thereon is shown illustrating the particular lateral armrest position.
Figure 61:
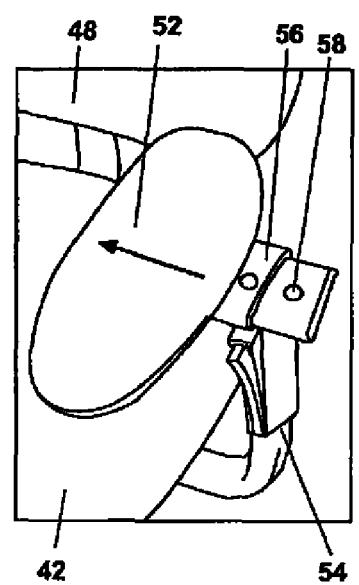
FIG. 61 shows the office chair of FIG. 57 with the armrest in a third lateral position, wherein an additional portion of the ergonomic marking thereon is shown illustrating the particular lateral armrest position.

Each of the adjusters 146, 50, 54 and 56 is provided with indicia 58 which are representative of the particular adjusted setting of the adjuster 46, 50, 54 and 56. The indicia 58 are preferably a series of color-coded symbols (such as circles as shown in the figures) which progressively increase or decrease in intensity and/or color so as to be indicative of the particular setting of the adjuster 46, 50, 54 and 56. For example, the indicia 58 in FIGS. 49-50 are representative of the height setting of the seat 42 relative to the base 44 as set by the seat height adjuster 46. The indicia 58 associated with the seatback height adjuster 50 are representative of the vertical height of the seatback 48 relative to the seat 42, and so forth.

The coding indicia 58 can take other forms, such as letters, numbers and the like without departing from the scope of this invention. Once the indicia 58 have been determined for each worker, a matrix can be determined to assist office managers in ensuring workers are using their equipment in an ergonomically-desirable manner. An example of such a settings matrix is set forth below.

| Worker | Seat Height Setting | Seatback Height Setting | Armrest Height Setting | Armrest Lateral Position Setting |
| --- | --- | --- | --- | --- |
| John S. | Blue | Blue | Green | Blue |
| Mary T. | Red | Orange | Blue | Orange |
| Joseph K. | Blue | Green | Green | Red |
| Susan F. | Orange | Green | Green | Yellow |

Furniture installers can also be provided the coded data by individual workstation to assure installation meets design criteria. A sales person or support group can provide the coded information to the workers, as well as training to help assure safe use of the product (e.g., to set chair heights and other adjustments to ergonomically correct settings for a particular worker).

The user's risk and/or safety teams can be provided the coded information to be used to audit compliance to safe work methods. Salespeople can utilize the system and method 10 provided to assess the potential risk of an installed customer to sell incremental products. Salespeople can also utilize the system and method 10 to sell furniture to high-risk individuals with pre-existing injuries or immediately following an injury to attempt to reduce the potential for future or exacerbating injuries. Product designers can utilize the system and method 10 to identify product niches not currently supported by product offerings and direct design efforts accordingly.

In the retail arena, the system and method 10 can be employed to assist retail purchasers in the selection of home office equipment which would tend to result in a selection of ergonomically-appropriate equipment for the home. A user-friendly interface, such as a touch-screen kiosk, could be provided in a retail establishment to allow users or retail salespeople to input required information (such as the attributes 14-18) of the system and method 10. The salespeople at the retail outlet can use the output 20 thereof to make sales recommendations or, alternatively, the system and method 10 can be interfaced with a database of office furniture products to provide a "shopping list" of appropriate products. An integrated sales and product promotion process is therefore provided, which can involve the entire distribution chain of the products at issue. A common language is utilized (measurement techniques) and processes for each person involved. A retailer is therefore provided with the opportunity to sell new discrete higher-priced and valued products to buyers, based on reduced risk and increased productivity as output by the coding equation 12.

While an office furniture-related example was discussed herein, the system and method 10 is equally applicable to any workplace arena, including manufacturing, plants and the like to assess the ergonomics of using punch and press equipment, for example, as well as lifting and equipment movement applications.

The system and method 10 can also be employed in safety audit applications. A user-friendly system and method 10 is provided to evaluate individuals and groups of individuals which considers people, tasks, and the environment in which work is performed. The coding equation 12 can provide quantified risk assessment, risk of injury, and productivity impact and can be independently validated through the coding indicia 58.

The inventive system and method 10 described herein measures attributes of the person, the task, and their environment, and to identify optimal outcomes and related risk-of-injury and productivity measures. The system and method 10 provides a vehicle to assess the ergonomic conditions and risk of injury of every employee in a company, if needed, and it is done in a user-friendly manner. In the safety audit arena, corporate risk and safety management teams or consultants can proactively assess a company's ergonomics situation and define an action plan to minimize risk.

The corporate risk and safety management teams or consultants can reactively investigate events and define an action plan to minimize risk. Additionally, teams for corporations that have home-based employees can identify when an off-site individual is at risk and requires an at-home visit or audit. Governmental risk and safety management teams can systematically assess the risk of an organization or investigate an incident, provide education, or impose fines based on the situation they find using the system and method 10 described herein. Labor unions can quantifiably assess the safety of the work environment of their members, and use that information to influence the actions of the employer.

While the invention has been specifically described in connection with certain specific embodiments thereof, it is to be understood that this is by way of illustration and not of limitation, and the scope of the appended claims should be construed as broadly as the prior art will permit.

The invention claimed is:

1. An apparatus for improving ergonomics for a user within a workplace, comprising:
   plurality of work areas, wherein a user can perform multiple physical tasks within the workplace by interacting with the plurality of work areas, each of the plurality of work areas having at least one physically adjustable parameter adjustable through a range of motion;
   an indicator associated with each of the plurality of work areas, the indicator comprising a series of visually unique settings, each setting corresponding to a physical range of motion of the at least one physically adjustable parameter of the corresponding plurality of work areas; and
   a stored data set associated with the user of the workplace, wherein the stored data set comprises information representative of a determined series of ergonomic settings for each of the at least one physically adjustable parameter of the plurality of work areas in the workplace as represented by the indicator and correlated with the user of the workplace;
   wherein retrieval of the stored data set corresponding to the user permits the plurality of work areas to be conformed to the determined series of ergonomic settings in the stored data set associated with the user of the workplace.

2. The apparatus of claim 1 wherein the determined series of ergonomic settings are based on input data representative of at least one of: (1) at least one physical characteristic of the user, (2) at least one physical characteristic of at least one task performed by the user, and (3) at least one physical characteristic of at least one environmental feature of the workplace.

3. The apparatus of claim 2 wherein the input data is input into at least one function and an output of the at least one function is used to determine a first series of fit settings for each of the plurality of work areas in the workplace.

4. The apparatus of claim 3 wherein the first series of fit settings is used to determine the series of ergonomic settings corresponding to the user of the workplace.

5. The apparatus of claim 1 wherein the workplace comprises an office environment.

6. The apparatus of claim 5 wherein at least one of the work areas comprises a keyboard located on an adjustable support tray having at least one physically adjustable parameter.

7. The apparatus of claim 5 wherein at least one of the work areas comprises a chair having a plurality of physically adjustable parameters.

8. The apparatus of claim 5 wherein at least one of the work area comprises a monitor mounted on a stand having at least one physically adjustable parameter.

9. The apparatus of claim 5 wherein the workplace comprises a home office.

10. The apparatus of claim 1 wherein the workplace comprises a manufacturing facility.

11. The apparatus of claim 10 wherein the work area comprises at least one of a work station, an assembly station, a computer work station and combinations thereof.

12. The apparatus of claim 1 wherein the at least one physically adjustable parameter comprises at least one of a seat height of a chair, an arm height of a chair, a monitor position, a leg position, a thigh position, an arm width adjustment of a chair, a lumbar height adjustment of a chair, a tilt lock adjustment of a chair, seat depth adjustment of a chair, a work surface height, a keyboard height, an input device position, a document holder position, a telephone position, a telephone use position, a foot rest position, a task position and combinations thereof.

13. The apparatus of claim 1 wherein the at least one physically adjustable parameter is adjustable through a range of motion having a first end and a second end and the series of visually unique settings comprises a first unique setting generally associated with a portion of the range of motion adjacent the first end, a second unique setting generally associated with a portion of the range of motion adjacent the second end, and at least one intervening unique setting between the first unique setting and the second unique setting.

14. The apparatus of claim 1 wherein each visually unique setting is color-coded to be visually distinct from the other of the visually unique settings.

15. The apparatus of claim 1 wherein the stored data set includes a matrix of determined ergonomic settings to which each of the at least one users is coded corresponding to each of the at least one physically adjustable parameters.

16. The apparatus of claim 1 wherein the visually unique settings of the indicator are visually perceptible from a distance to allow for easy visual auditing of the alignment of the at least one physically adjustable parameter of the plurality of work areas with the determined series of ergonomic settings corresponding to the user in the work area.

17. The apparatus of claim 1 wherein the visually unique settings of the indicator include sub-graduated areas corresponding to additional ergonomic settings.

* * * * *

UNITED STATES PATENT AND TRADEMARK OFFICE
CERTIFICATE OF CORRECTION

PATENT NO. : 8,195,475 B1
APPLICATION NO. : 10/250095
DATED : June 5, 2012
INVENTOR(S) : James Landsman et al.

It is certified that error appears in the above-identified patent and that said Letters Patent is hereby corrected as shown below:

The following paragraphs are to be inserted at Column 4, line 65, following the "Summary of Invention" heading and prior to the first paragraph.

-- In one aspect, the invention relates to an apparatus for improving ergonomics for a user within a workplace comprising a plurality of work areas, wherein a user can perform multiple physical tasks within the workplace by interacting with the plurality of work areas, each of the plurality of work areas having at least one physically adjustable parameter adjustable through a range of motion. The apparatus further comprises an indicator associated with each of the plurality of work areas, the indicator comprising a series of visually unique settings, each setting corresponding to a physical range of motion of the at least one physically adjustable parameter of the corresponding plurality of work areas, and a stored data set associated with at least one user of the workplace. The stored data set comprises information representative of a determined series of ergonomic settings for each of the at least one physically adjustable parameter of the plurality of work areas in the workplace as represented by the indicator and correlated with the at least one user of the workplace. Retrieval of the stored data set corresponding to the at least one user permits the plurality of work areas to be conformed to the determined series of ergonomic settings in the stored data set associated with the at least one user of the workplace.

In another aspect, the determined series of ergonomic settings are based on input data representative of at least one of: (1) at least one physical characteristic of a user, (2) at least one physical characteristic of at least one task performed by the user, and (3) at least one physical characteristic of at least one environmental feature of the workplace. The input data can be input into at least one function and an output of the at least one function is used to determine a first series of fit settings for each of the plurality of work areas in the workplace. The first series of fit settings can be used to determine the series of ergonomic settings corresponding to the at least one user of the workplace.

According to another aspect of the invention, the workplace comprises an office environment. At least one of the work areas can comprise a keyboard located on an adjustable support tray having at least one physically adjustable parameter. At least one of the work areas can comprise a chair having a plurality of physically adjustable parameters. At least one of the work areas can comprise a monitor Signed and Sealed this
Seventh Day of August, 2012

David J. Kappos
*Director of the United States Patent and Trademark Office* mounted on a stand having at least one physically adjustable parameter. The workplace can comprise a home office.

According to another aspect, the workplace comprises a manufacturing facility. The work area can comprise at least one of a work station, an assembly, station, a computer work station and combinations thereof.

According to yet another aspect, the at least one physically adjustable parameter comprises at least one of a seat height of a chair, an arm height of a chair, a monitor position, a leg position, a thigh position, an arm width adjustment of a chair, a lumbar height adjustment of a chair, a tilt lock adjustment of a chair, seat depth adjustment of a chair, a work surface height, a keyboard height, an input device position, a document holder position, a telephone position, a telephone use position, a foot rest position, a task position and combinations thereof.

According to another aspect, the at least one physically adjustable parameter is adjustable through a range of motion having a first end and a second end and the series of visually unique settings comprises a first unique setting generally associated with a portion of the range of motion adjacent the first end, a second unique setting generally associated with a portion of the range of motion adjacent the second end, and at least one intervening unique setting between the first unique setting and the second unique setting.

According to yet another aspect, each visually unique setting is color-coded to be visually distinct from the other of the visually unique settings.

In yet another aspect, the stored data set includes a matrix of determined ergonomic settings to which each of the at least one users is coded corresponding to each of the at least one physically adjustable parameters.

In another aspect, the visually unique settings of the indicator are visually perceptible from a distance to allow for easy visual auditing of the alignment of the at least one physically adjustable parameter of the plurality of work areas with the determined series of ergonomic settings corresponding to the at least one user in the work area.

According to another aspect, the visually unique settings of the indicator include sub-graduated areas corresponding to additional ergonomic settings. --